United States Patent
Gill et al.

(10) Patent No.: US 10,662,221 B2
(45) Date of Patent: May 26, 2020

(54) CYSTARGOLIDE COMPOUNDS AND USES THEREOF

(71) Applicant: UNIVERSITY OF PRINCE EDWARD ISLAND, Charlottetown (CA)

(72) Inventors: Krista Ann Gill, Bradford (CA); Fabrice Berrue, Charlottetown (CA); Russell Greig Kerr, Charlottetown (CA)

(73) Assignee: UNIVERSITY OF PRINCE EDWARD ISLAND (CA)

( * ) Notice: Subject to any disclaimer, the term of this patent is extended or adjusted under 35 U.S.C. 154(b) by 0 days.

(21) Appl. No.: 15/548,241

(22) PCT Filed: Feb. 2, 2016

(86) PCT No.: PCT/CA2016/050085
§ 371 (c)(1),
(2) Date: Aug. 2, 2017

(87) PCT Pub. No.: WO2016/123699
PCT Pub. Date: Aug. 11, 2016

(65) Prior Publication Data
US 2018/0155392 A1   Jun. 7, 2018

Related U.S. Application Data

(60) Provisional application No. 62/111,401, filed on Feb. 3, 2015.

(51) Int. Cl.
| | |
|---|---|
| *C07K 5/06* | (2006.01) |
| *C07K 5/062* | (2006.01) |
| *A61P 35/00* | (2006.01) |
| *A61K 38/00* | (2006.01) |

(52) U.S. Cl.
CPC .......... *C07K 5/06052* (2013.01); *A61P 35/00* (2018.01); *A61K 38/00* (2013.01)

(58) Field of Classification Search
None
See application file for complete search history.

(56) References Cited

PUBLICATIONS

Gill K et al., "Discovery of new peptide natural products from Actinobacteria". 2014 Science Graduate Studies Day, May 23, 2014 (May 23, 2014), (abstract) [online] [retrieved on Feb. 26, 2016 (Feb. 26, 2016)]. http://files.upei.ca/science/graduatestudies/graduateday abstracts 2014.pdf.*
Gill et al. Cystargolides, 20S Proteasome Inhibitors Isolated from Kitasatospora cystarginea. J Nat Prod. Apr. 24, 2015;78(4):822-6. https://www.ncbi.nlm.nih.gov/pubmed/25769015.*
Tello-Aburto et al. Total synthesis and absolute stereochemistry of the proteasome inhibitors cystargolides A and B. Org. Biomol. Chem., 2015,13, 10127-10130. https://pubs.rsc.org/en/content/articlepdf/2015/ob/c5ob01821h.*
International Search Report for PCT /CA2016/050085; 2 pgs.
Written Opinion PCT /CA2016/050085; 5 pgs.
Gill KA et al., "*Cystargolides, 20S proteasome inhibitors isolated from Kitasatospora 1-7 cystarginea*". J Nat Prod., Mar. 13, 2015 (Mar. 13, 2015), vol. 78(4), pp. 822-826. The whole document.
Tello-Aburto R et al., "*Total synthesis and absolute stereochemistry of the proteasome 1-7 inhibitors cystargolides A and B*". Organic & Biomolecular Chemistry, Sep. 17, 2015 (Sep. 17, 2015), vol. 13(40), pp. 10127-10130. The whole document.
Gill K et al., "*Discovery of new peptide natural products from Actinobacteria*". 2014 Science Graduate Studies Day, May 23, 2014 (May 23, 2014), (abstract) [online] [retrieved on Feb. 26, 2016 (Feb. 26, 2016)]. Retrieved from the Internet: <http://files.upei.ca/science/graduatestudies/graduate_day_abstracts_2014.pdf>.

* cited by examiner

Primary Examiner — Maury A Audet
(74) Attorney, Agent, or Firm — Schmeiser, Olsen & Watts, LLP

(57) ABSTRACT

There is provided herein compounds of formula I, wherein $R_1$ is H or linear or branched $C_1$-$C_6$ lower alkyl; $R_2$ is H, linear or branched $C_1$-$C_6$ lower alkyl, or a proteinogenic amino acid side chain; $R_3$ is H, linear or branched $C_1$-$C_6$ lower alkyl, or a proteinogenic amino acid side chain; $R_4$ is —OH or —O—$R_5$ wherein $R_5$ is linear or branched $C_1$-$C_6$ lower alkyl; and each $R_6$ is independently H or —$CH_3$; or a pharmaceutically acceptable prodrug, salt, or ester thereof. Compositions containing said compounds, and uses thereof, are also provided.

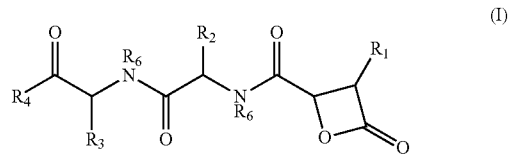

10 Claims, 24 Drawing Sheets

CYSTARGOLIDE COMPOUNDS AND USES THEREOF

CROSS-REFERENCE TO RELATED APPLICATIONS

This application claims priority to PCT Application No. PCT/CA2016/050085, having a filing date of Feb. 2, 2016, based off of U.S. Provisional Application No. 62/111,401 having a filing date of Feb. 3, 2015, the entire contents both of which are hereby incorporated by reference.

FIELD OF TECHNOLOGY

The following relates generally to compounds isolated from *Kitasatospora cystarginea*, and analogues thereof. More specifically, the following relates to cystargolide compounds and uses thereof.

BACKGROUND

Many clinically approved drugs originated from natural products. Well-known examples include morphine, penicillin, Yondelis, and erythromycin. Natural product drugs have been isolated from plants, fungus, marine invertebrates, and bacteria.

Actinobacteria are gram-positive, soil-dwelling bacteria. Actinomycetes have been described as the most prolific source of bioactive microbial natural products, making them a valuable resource for the discovery of new secondary metabolites. Members of the genus *Kitasatospora*, which are classified as rare Actinobacteria, have been shown to produce a wide variety of natural products including bafilomycins, kitasetaline and more recently satosporins.[4] Members of this rare and underexplored genus have the potential to produce multiple natural products, which was revealed by genome sequencing of *Kitasatospora setae* showing the presence of 24 putative secondary metabolite gene clusters. This makes members of this genus ideal microorganisms to investigate for their ability to produce structurally unique and bioactive secondary metabolites.

*Kitasatospora cystarginea* NRRL-B16505 is a soil dwelling bacterium that was originally isolated in 1988 from Yamaguchi Prefecture, Japan, and was reported to produce the antifungal peptide cystargin. It has also recently been reported to produce the cyclic lipopeptide cystargamide.

The β-lactone class of natural products is a broad class that has a variety of biological activities. Tetrahydroxylipstatin (THL, Orlistat) is a derivative of the natural product lipstatin, and is a β-lactone containing compound that is approved by the FDA as a pancreatic lipase inhibitor used to treat obesity. Other members of this class include belactosin A, salinosporamide A and omuralide, which are all reported to have proteasome inhibitory activity.

The ubiquitin-proteasome pathway plays a major role in eukaryotic cellular protein degradation. This system adjusts the level of proteins involved in regulating cellular processes like signal transduction, immune responses and cell cycle progression. Inhibitors of the proteasome have gained attention for their ability to block cell cycle progression and cause apoptosis, which makes them useful antiproliferative agents. Bortezomib and carfilzomib are proteasome inhibitors that have been approved by the FDA for treatment of multiple myeloma, and several other proteasome inhibitors are currently in clinical trials.

A need exists for additional, alternative, and/or improved natural product-based compounds having biological activity.

SUMMARY

An aspect relates to a compound of formula I:

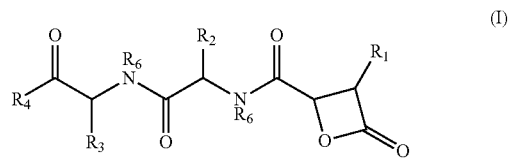

wherein $R_1$ is H or linear or branched $C_1$-$C_6$ lower alkyl; $R_2$ is H, linear or branched $C_1$-$C_6$ lower alkyl, or a proteinogenic amino acid side chain; $R_3$ is H, linear or branched $C_1$-$C_6$ lower alkyl, or a proteinogenic amino acid side chain; $R_4$ is —OH or —O—$R_5$ wherein $R_5$ is linear or branched $C_1$-$C_6$ lower alkyl; and each $R_6$ is independently H or —CH$_3$, or a pharmaceutically acceptable prodrug, salt, or ester thereof.

In a further embodiment, there is provided a compound having the following formula:

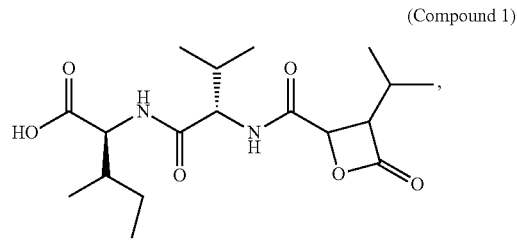 [SMILES: CCC(C)[C@H](NC(=O)[C@@H](NC(=O)C1OC(=O)C1C(C)C)C(C)C)C(=O)O]

(Compound 1)

or a pharmaceutically acceptable prodrug, salt, or ester thereof.

In yet another embodiment, there is provided a compound having the following formula:

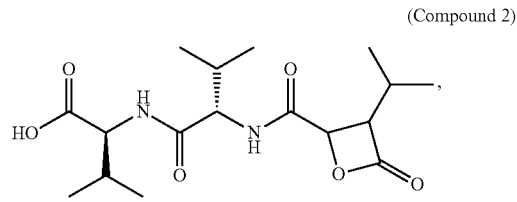 [SMILES: CC(C)C1C(=O)OC1C(=O)N[C@H](C(=O)N[C@H](C(=O)O)C(C)C)C(C)C]

(Compound 2)

or a pharmaceutically acceptable prodrug, salt, or ester thereof.

In a further embodiment, there is provided a composition comprising a compound as described above, and a pharmaceutically acceptable carrier, diluent, or excipient.

In an embodiment, there is provided herein a use of the compound as outlined herein, or the composition as outlined herein, for inhibiting 20S proteasome.

In another embodiment, there is provided herein a use of the compound as outlined herein, or the composition as outlined herein, for inhibiting cell proliferation.

In still another embodiment, there is provided herein a use of the compound as outlined herein, or the composition as outlined herein, for the treatment of cancer.

Other features and advantages of the present application will become apparent from the following detailed description. It should be understood, however, that the detailed description and the specific examples below are non-limiting embodiments of the application, and are given by way of illustration only, since various changes and modifications will become apparent to those skilled in the art having regard to this application.

BRIEF DESCRIPTION

Some of the embodiments will be described in detail, with references to the following figures, wherein like designations denote like members, wherein:

FIG. 1 shows prioritization of *K. cystarginea* B16505 based on LC-HRMS/PCA dereplication. PCA scores plot (PC-1 vs. PC-2) showed replicates of *K. cystarginea* (16505) as outliers from the other 11 strains. PCA loadings plot (PC-1 vs. PC-2) showed that the presence of bucket values m/z=357.2021, $R_T$=2.8 and m/z=371.2177, $R_T$=3.0 are contributing to the observed variation between the chemical profiles;

DETAILED DESCRIPTION

Figure 1:
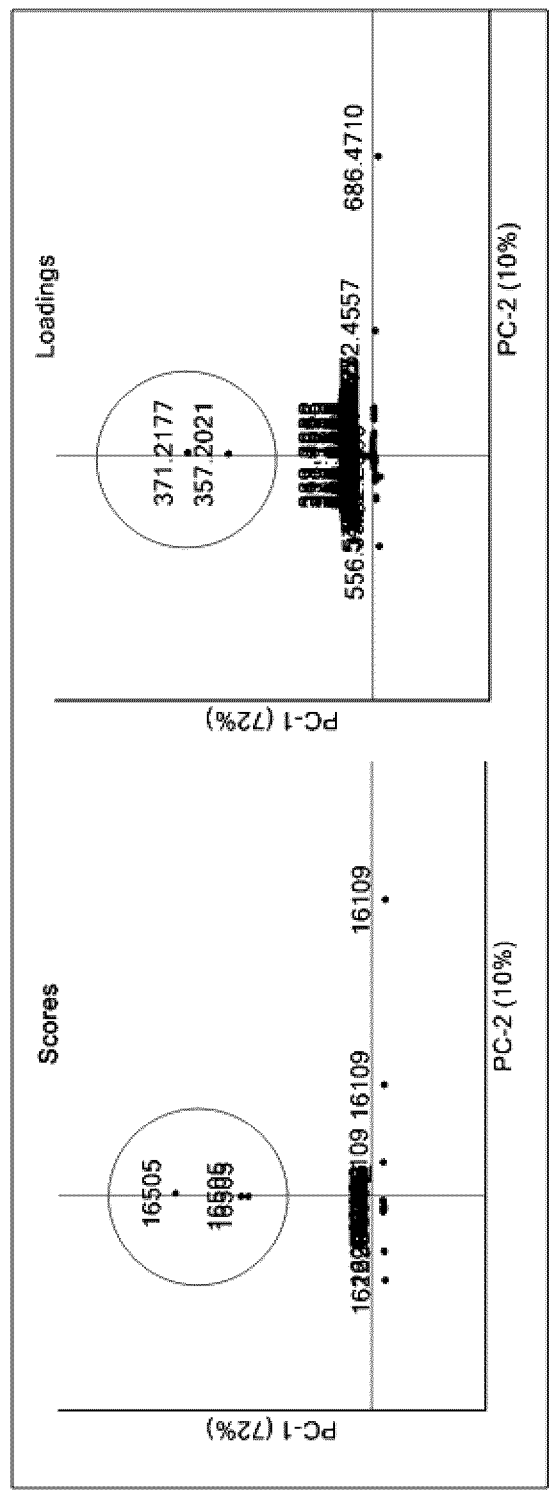

Described herein are *Kitasatospora cystarginea*-derived compounds, compositions, analogues thereof, and uses thereof. In certain embodiments, compounds of formula I are provided:

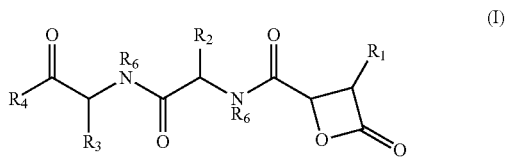

wherein $R_1$ is H or linear or branched $C_1$-$C_6$ lower alkyl; $R_2$ is H, linear or branched $C_1$-$C_6$ lower alkyl, or a proteinogenic amino acid side chain; $R_3$ is H, linear or branched $C_1$-$C_6$ lower alkyl, or a proteinogenic amino acid side chain; $R_4$ is —OH or —O—$R_5$ wherein $R_5$ is linear or branched $C_1$-$C_6$ lower alkyl; and each $R_6$ is independently H or —$CH_3$, or a pharmaceutically acceptable prodrug, salt, or ester thereof.

It will be understood that a proteinogenic amino acid side chain may include any suitable naturally occurring, or artificial, amino acid side chain known to the person of skill in the art.

Compounds may be provided as a mixture of stereoisomers; may be partially, substantially, or fully enriched in one stereoisomer; or may be provided in pure enantiomeric/diastereomeric/stereoisomeric form.

The described compounds can be provided in pharmaceutical compositions together with an acceptable diluents, carrier, or excipient, and/or together with one or more separate active agents or drugs as part of a pharmaceutical combination. In addition, the pharmaceutical compositions may be administered in a treatment regime with other drugs or pharmaceutical compositions, either separately or in a combined formulation or combination.

A composition of embodiments of the present invention may be formulated with a vehicle or carrier pharmaceutically acceptable for administration to a subject, for example a human, in need thereof. Methods of formulation for such compositions are well known in the art and taught in standard reference texts such as Remington's Pharmaceutical Sciences, Mack Publishing Co., Easton, Pa., 1985. A composition of embodiments of the present invention may comprise a single compound, or a combination thereof. Compositions of embodiments of the present invention may be administered alone, or in combination with a second drug or agent.

It will be understood that analogues of the compounds may be possible. Analogues may include, but are not limited to, prodrug forms, physiologically functional derivatives, and bioisosteres of compounds provided herein.

Physiologically functional derivatives or prodrugs may include any pharmaceutically acceptable derivative of a compound as described herein, for example, an ester or an amide, which upon administration to a mammal is capable of providing (directly or indirectly) a compound of embodiments of the present invention, or an active metabolite thereof. Such derivatives are clear to those skilled in the art, without undue experimentation, and with reference to, for example, the teaching of Burger's Medicinal Chemistry And Drug Discovery, 5.sup.th Edition, Vol 1: Principles and Practice, which is incorporated herein by reference to the extent that it teaches physiologically functional derivatives. Suitable pharmaceutically acceptable prodrugs will be well known to the person of skill in the art. One non-limiting example of a pharmaceutically acceptable prodrug may be a pharmaceutically acceptable ester derivative of a carboxylic acid-containing compound as described herein, such as an acetate ester.

It will also be understood that bioisosteres of the compounds may be possible. "Bioisosterism" is a lead modification approach used by those skilled in the art of drug design and shown to be useful in attenuating toxicity and modifying activity of a lead compound. Bioisosteric approaches are discussed in detail in standard reference texts such as The Organic Chemistry of Drug Design and Drug Action (Silverman, R B, Academic Press, Inc. 1992 San Diego, Calif., pages 19-23).

It will be understood that alkyl groups may either be unsubstituted or substituted with one or more substituents, e.g. halogen, alkyl, alkylene, alkoxy, alkylthio, trifluoromethyl, acyloxy, hydroxy, mercapto, carboxy, aryloxy, aryl, arylalkyl, heteroaryl, amino, alkylamino, dialkylamino, morpholino, piperidino, pyrrolidin-1-yl, piperazin-1-yl, or other functionality.

The term "lower alkyl" may refer to a cyclic, branched or straight/linear chain monovalent alkyl moiety of one to six carbon atoms. This term is further exemplified by such moieties as methyl, ethyl, n-propyl, i-propyl, n-butyl, t-butyl, i-butyl (or 2-methylpropyl), cyclopropylmethyl, i-amyl, n-amyl, and hexyl. Lower alkyl groups can also be unsubstituted or substituted, as described immediately above.

Salts of the compounds may also be possible. Salts may include those which are suitable for, or compatible with, the treatment of patients, and may include any non-toxic organic or inorganic salt. The selection of the appropriate salt will be known to one skilled in the art. By way of non-limiting example, sodium or potassium salts of the compounds provided herein, of HCl salts of the compounds provided herein, may be possible.

Solvates of the compounds may also be possible. Solvates may include a solvate of a compound or its pharmaceutically acceptable salt, wherein molecules of a suitable solvent are incorporated in the crystal lattice. A suitable solvent may be physiologically tolerable at the dosage administered. Examples of suitable solvents may be ethanol, water and the like. When water is the solvent, the molecule may be referred to as a "hydrate". The formation of solvates may vary depending on the compound and the solvate. In general, solvates are formed by dissolving the compound in the appropriate solvent and isolating the solvate by cooling or using an antisolvent. The solvate may be dried or azeotroped under ambient conditions.

In certain embodiments, the compounds described herein have at least one asymmetric center. These compounds exist as enantiomers. Where compounds possess more than one asymmetric center, they may exist as diastereomers. It is to be understood that all such isomers and mixtures thereof in any proportion are encompassed within the scope of the present application. It is to be further understood that while the stereochemistry of the compounds may be as shown in any given compound listed herein, such compounds may also contain certain amounts (e.g. less than 20%, suitably less than 10%, more suitably less than 5%) of compounds of the application having alternate stereochemistry. For example, compounds of the application that are shown without any stereochemical designations are understood to be racemic mixtures (i.e. contain an equal or substantially equal amount/mixture of each possible enantiomer or diastereomer). However, it is to be understood that all enantiomers and diastereomers are included within the scope of the present application, including mixtures thereof in any proportion.

It will be understood that reference to treating or treatment may refer to an approach for obtaining beneficial or desired results, including clinical results. Beneficial or desired clinical results may include, but are not limited to, alleviation or amelioration of one or more symptoms or conditions, diminishment of extent of disease, stabilized (i.e. not worsening) state of disease, preventing spread of disease, delay or slowing of disease progression, amelioration or palliation of the disease state, diminishment of the reoccurrence of disease, and remission (whether partial or total), whether detectable or undetectable. Treating and treatment may also mean prolonging survival as compared to expected survival if not receiving treatment, and may also include prophylactic treatment.

Treatment methods may comprise administering to a subject a therapeutically effective amount of one or more of the compounds of the application and optionally consists of a single administration, or alternatively comprises a series of administrations. As used herein, the term "effective amount" or "therapeutically effective amount" means an amount effective, at dosages and for periods of time necessary to achieve the desired result. Effective amounts may vary according to factors such as the disease state, age, sex and/or weight of the subject. The amount of a given compound that will correspond to such an amount may vary depending upon various factors, such as the given drug or compound, the pharmaceutical formulation, the route of administration, the type of condition, disease or disorder, the identity of the subject being treated, and the like, but can nevertheless be routinely determined by one skilled in the art.

Reference to preventing or prevention may mean at least partially delaying or reducing the likelihood of developing a disease, disorder, or condition, or at least one symptom or aspect of a disease, disorder, or condition.

As referred to herein, a pharmaceutically acceptable carrier, diluent, or excipient may include any suitable carriers, diluents, or excipients known to the person of skill in the art. Examples of pharmaceutically acceptable excipients may include, but are not limited to, cellulose derivatives, sucrose, and starch. The person of skill in the art will recognize that pharmaceutically acceptable excipients may include suitable fillers, binders, lubricants, glidants, and disentegrants known in the art (see, for example, Remington: The Science and Practice of Pharmacy (2006)). Examples of pharmaceutically acceptable carriers, diluents, and excipients may be found in, for example, Remington's Pharmaceutical Sciences (2000-20th edition) and in The United States Pharmacopeia: The National Formulary (USP 24 NF19) published in 1999.

The compounds of the application may be suitably formulated into pharmaceutical compositions for administration to subjects in a biologically compatible form suitable for administration in vivo. Accordingly, the present application may include a pharmaceutical composition comprising one or more compounds of the application and a pharmaceutically acceptable carrier.

The compounds of the application may be administered to a subject in a variety of forms depending on the selected route of administration, as will be understood by those skilled in the art. A compound of the application may be administered, for example, by oral, parenteral, buccal, sublingual, nasal, rectal, patch, pump or transdermal administration and the pharmaceutical compositions formulated accordingly. Parenteral administration includes intravenous, intraperitoneal, subcutaneous, intramuscular, transepithelial, nasal, intrapulmonary, intrathecal, rectal and topical modes of administration. Parenteral administration may be by continuous infusion over a selected period of time. Conventional procedures and ingredients for the selection and preparation of suitable compositions are described, for example, in Remington's Pharmaceutical Sciences (2000-20th edition) and in The United States Pharmacopeia: The National Formulary (USP 24 NF19) published in 1999.

A compound of the application may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, the compound may be incorporated with excipient and used in the form of ingestible tablets, buccal tablets, troches, capsules, elixirs, suspensions, syrups, wafers, and the like. Oral dosage forms also include modified release, for example immediate release and timed-release, formulations. Examples of modified-release formulations include, for example, sustained release (SR), extended-release (ER, XR, or XL), time-release or timed-release, controlled-release (CR), or continuous-release (CR or Contin), employed, for example, in the form of a coated tablet, an osmotic delivery device, a coated capsule, a microencapsulated microsphere, an agglomerated particle, e.g., as of molecular sieving type particles, or, a fine hollow permeable fiber bundle, or chopped hollow permeable fibers, agglomerated or held in a fibrous packet. In an embodiment, coatings that inhibit degradation of the compounds of the application by esterases, for example plasma esterases, are used in the oral administration forms. Timed-release compositions can be formulated, e.g. liposomes or those wherein the active compound is protected with differentially degradable coatings, such as by microencapsulation, multiple coatings, etc. Liposome delivery systems include, for example, small unilamellar vesicles, large unilamellar vesicles and multilamellar vesicles. Liposomes can be formed from a variety of phospholipids, such as cholesterol, stearylamine or phosphatidylcholines.

It may also possible to freeze-dry the compounds of the application and use the lyophilizates obtained, for example, for the preparation of products for injection.

A compound of the application may also be administered parenterally. Solutions of a compound of the application can be prepared in water suitably mixed with a surfactant such as hydroxypropylcellulose. Dispersions can also be prepared in glycerol, liquid polyethylene glycols, DMSO and mixtures thereof with or without alcohol, and in oils. Under ordinary conditions of storage and use, these preparations contain a preservative to prevent the growth of microorganisms. A person skilled in the art would know how to prepare suitable formulations.

The pharmaceutical forms suitable for injectable use include sterile aqueous solutions or dispersions and sterile powders for the extemporaneous preparation of sterile injectable solutions or dispersions. The form may be sterile and may be fluid to the extent that easy syringability exists.

Compositions for nasal administration may conveniently be formulated as aerosols, drops, gels and powders. Aerosol formulations typically comprise a solution or fine suspension of the active substance in a physiologically acceptable aqueous or non-aqueous solvent and are usually presented in single or multidose quantities in sterile form in a sealed container, which can take the form of a cartridge or refill for use with an atomising device. Alternatively, the sealed container may be a unitary dispensing device such as a single dose nasal inhaler or an aerosol dispenser fitted with a metering valve which is intended for disposal after use. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomizer.

Compositions suitable for buccal or sublingual administration include tablets, lozenges, and pastilles, wherein the active ingredient is formulated with a carrier such as sugar, acacia, tragacanth, or gelatin and glycerine. Compositions for rectal administration are conveniently in the form of suppositories containing a conventional suppository base such as cocoa butter.

Compounds of the application may also be delivered by the use of monoclonal antibodies as individual carriers to which the compound molecules are coupled. Compounds of the application may also be coupled with soluble polymers as targetable drug carriers. Such polymers can include polyvinylpyrrolidone, pyran copolymer, polyhydroxypropylmethacrylamide-phenol, polyhydroxy-ethylaspartamide-phenol, or polyethyleneoxide-polylysine substituted with palmitoyl residues. Furthermore, compounds of the application may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and crosslinked or amphipathic block copolymers of hydrogels.

When compounds are used in combination with other agents useful in treating diseases, disorders or conditions, it is an embodiment that the compounds of the application are administered contemporaneously with those agents. As used herein, "contemporaneous administration" of two substances to a subject means providing each of the two substances so that they are both biologically active in the individual at the same time. The exact details of the administration will depend on the pharmacokinetics of the two substances in the presence of each other, and can include administering the two substances within a few hours of each other, or even administering one substance within 24 hours of administration of the other, if the pharmacokinetics are suitable. Design of suitable dosing regimens is routine for one skilled in the art. In particular embodiments, two substances will be administered substantially simultaneously, i.e., within minutes of each other, or in a single composition that contains both substances. It is a further embodiment of the present application that a combination of agents is administered to a subject in a non-contemporaneous fashion.

The dosage of compounds of the application can vary depending on many factors such as the pharmacodynamic properties of the compound, the mode of administration, the age, health and weight of the recipient, the nature and extent of the symptoms, the frequency of the treatment and the type of concurrent treatment, if any, and the clearance rate of the compound in the subject to be treated. One of skill in the art can determine the appropriate dosage based on the above factors. Compounds of the application may be administered initially in a suitable dosage that may be adjusted as required, depending on the clinical response. As a representative example, oral dosages of one or more compounds of the application will range between about 1 mg per day to about 1000 mg per day for an adult, suitably about 1 mg per day to about 500 mg per day, more suitably about 1 mg per day to about 200 mg per day. In an embodiment of the application, compositions are formulated for oral administration and the compounds are suitably in the form of tablets containing 0.25, 0.5, 0.75, 1.0, 5.0, 10.0, 20.0, 25.0, 30.0, 40.0, 50.0, 60.0, 70.0, 75.0, 80.0, 90.0, 100.0, 150, 200, 250, 300, 350, 400, 450, 500, 550, 600, 650, 700, 750, 800, 850, 900, 950 or 1000 mg of active ingredient per tablet. Compounds of the application may be administered in a single daily dose or the total daily dose may be divided into two, three or four daily doses.

The compounds of the present application may be useful as medicaments. Accordingly the application also includes a compound of the application for use as a medicament.

Treatment or prevention methods may comprise administering to a subject or a cell, a therapeutically effective amount of one or more of the compounds of the application, and optionally consists of a single administration, or alternatively comprises a series of administrations.

The length of the treatment period depends on a variety of factors, such as the cause of the disease, disorder or condition, severity of the disease, disorder or condition, the age of the subject, the concentration of the compound, the activity of the compound, and/or a combination thereof. It will also be appreciated that the effective dosage of the compound used for the treatment or prevention may increase or decrease over the course of a particular treatment or prevention regime. Changes in dosage may result and become apparent by standard diagnostic assays known in the art. In some instances, chronic administration may be required. For example, the compounds are administered to the subject in an amount and for a duration sufficient to treat the subject.

In an embodiment, compounds as disclosed herein may inhibit human 20S proteasome. In a further embodiment, compounds as disclosed herein may inhibit cell proliferation. In another embodiment, compounds as disclosed herein may be used to inhibit, treat, or prevent cancer in vitro or in vivo.

Cystargolides

Disclosed herein are Cystaroglide compounds and uses thereof. Examples of Cystaroglides may include Cystargolides A (1) and B (2), which are new β-lactone containing peptide natural products.

As described herein, Cystargolides A (1) and B (2) were discovered using a chemical screening technique that combines LC-HRMS with principal component analysis (PCA). This method allows for efficient prioritization of bacterial strains based on their unique chemical profiles. Compounds 1 and 2 were isolated from the fermentation broth of *Kitasatospora cystarginea*, and their structures were elucidated using NMR spectroscopy and mass spectrometry. As shown herein, these compounds inhibit human 20S proteasome, and may represent candidates for structural optimization to maximize inhibition of cell proliferation.

Examples

Cystaroghde A (1) and B (2)

Twelve strains of the genus *Kitasatospora* were fermented and the chemical composition of each extract was assessed using an LC-HRMS based metabolomics approach, in which principal component analysis (PCA) allowed rapid identification of the presence of putatively novel chemical entities.[8,9]

As described herein, isolation and structure elucidation of two novel β-lactone containing natural products, cystargolides A (1) and B (2), that exhibit inhibitory activity in a 20S proteasome assay, was performed. The cystargolides are β-lactone containing metabolites with a 3-isopropyl-4-oxooxetate-2-carboxyl moiety.

Metabolomic Screening and Purification:

Twelve strains of *Kitasatospora* spp. were cultured in triplicate for 72 hours in a nutrient lean medium. Fermentation broths were extracted with ethyl acetate, and the resulting organic extracts were analyzed by LC-HRMS. The data processing prior to statistical analysis was performed according to the previously described procedure. Principal component analysis was used to interrogate the secondary metabolomes of each bacterial strain and highlighted *K. cystarginea* NRRL-B16505 as a producer of putatively novel natural products. The visualization of the scores plot PC-1 vs PC-2 rapidly indicated that the three replicate extracts were separated from the rest of the samples, while the corresponding loadings plot revealed the variables (retention time-m/z) responsible for the observed discrimination (see FIG. 1).

Two metabolites defined by the buckets (3.0 min, m/z 371.2177 $[M+H]^+$) and (2.8 min, m/z 357.2021 $[M+H]^+$) were therefore identified as compounds solely produced by the strain *K. cystarginea* (16505). Database searches (AntiBase 2012)[27] for the exact masses of these protonated adducts returned no matches, which led to a further chemical investigation of *K. cystarginea* metabolomes. Scale-up fermentation was undertaken, culture broths were extracted with ethyl acetate, and the resulting organic extract was fractionated by $C_{18}$ liquid chromatography and further purified using RP-HPLC with a phenyl hexyl stationary phase to yield 2.5 mg and 3.1 mg of cystargolides A (1) and B (2), respectively.

Figure 2:
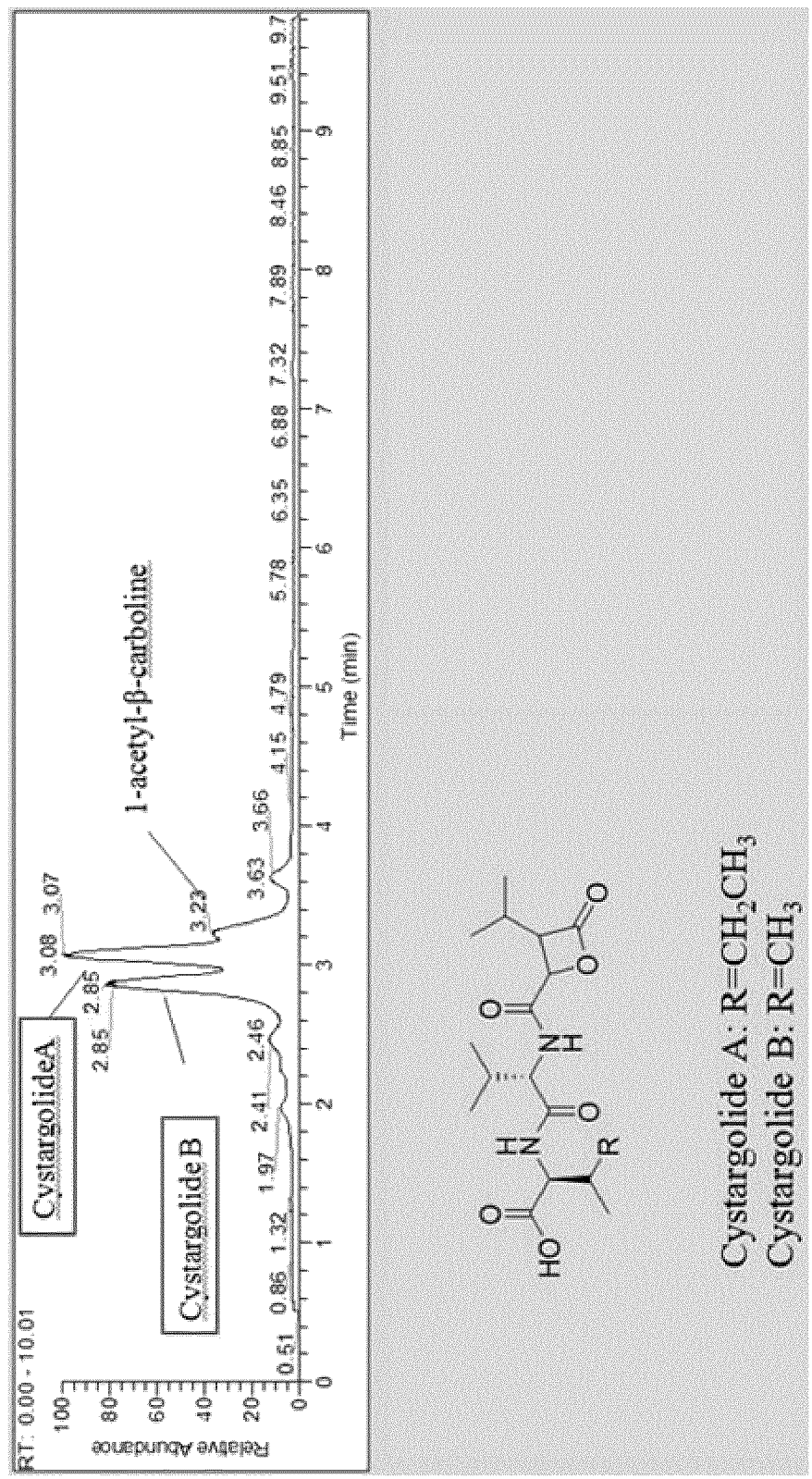
FIG. 2 shows HPLC separation of compounds obtained from *K. cystarginea*.

Separation of compounds obtained from *K. cystarginea* can be achieved using HPLC, as shown in FIG. 2.

Structure Elucidation:

Cystargolide A (1) was isolated as a pale yellow powder, and HRESIMS supported a molecular formula of $C_{18}H_{30}N_2O_6$ (m/z 371.2177 $[M+H]^+$, Δ=0.1 ppm), indicating five degrees of unsaturation. The NMR data (Table 1) revealed the presence of four carbonyls accounting for four of the five degrees of unsaturation in addition to two amide proton signals, which suggested that compound 1 was a peptide. Two amino acids were recognized as isoleucine and valine by interpretation of the $^1H$-$^1H$ COSY correlations identifying the two peptidic spin systems $NH_a$ ($(\delta_H 8.12)$ to $H_3$-6 ($\delta_H$ 0.82) and $NH_b$ ($\delta_H$ 8.53) to $H_3$-5' ($\delta_H$ 0.81).

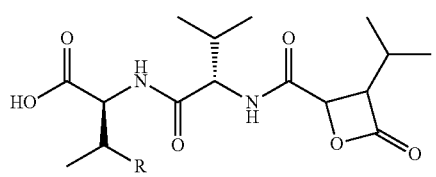

Cystargolide A 1 R = CH$_2$CH$_3$
Cystargolide B 2 R = CH$_3$

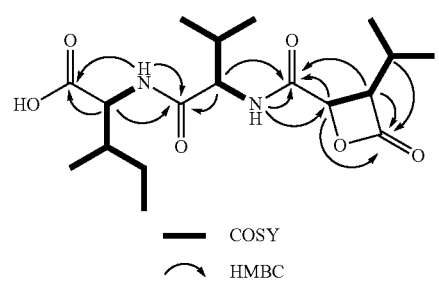

— COSY
⌒ HMBC

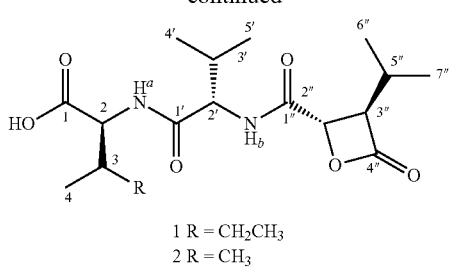

1 R = CH₂CH₃
2 R = CH₃

In a similar manner, COSY correlations were used to assign the third spin system H-2" ($\delta_H$ 5.01) to H$_3$-7" ($\delta_H$ 0.97). Key HMBC correlations between H-2"/C-1" ($\delta_C$ 167.3), C-4" ($\delta_C$ 169.8); H-3" ($\delta_H$ 3.50)/C-1", C-4" and H-5" ($\delta_H$ 2.11)/C-4" unambiguously located the two carbonyl functional groups in position C-1" and C-4", respectively. The de-shielded resonances at $\delta_H$ 5.01 (H-2") and $\delta_C$ 69.9 (C-2") suggested that C-2" was attached to an oxygen atom. The connectivity between the isoleucine, valine and the third spin system was determined based on the key HMBC correlations H-2 ($\delta_H$ 4.16), NH$_a$/C-1 ($\delta_C$ 172.8); H-2, NH$_a$, H-2' $\delta_H$ 4.37)/C-1' ($\delta_C$ 170.5); H-2', NH$_b$, H-2", H-3"/C-1"; and NH$_b$/C-2" ($\delta_C$ 70.0). NOESY data supported the amino acid sequence assignment and showed strong correlations between NH$_a$ ($\delta_H$ 8.12)/H-2' ($\delta_H$ 4.37); NH$_b$ ($\delta_H$ 8.53)/H-2" ($\delta_H$ 5.01), which was also supported by tandem mass spectrometry and the specific fragmentation pattern.

The fifth degree of unsaturation was attributed to cyclization. Two options were therefore available; a macrolactone cyclization between C-1 and the C-2" hydroxyl, or a β-lactone between C-4" and the C-2" hydroxyl. The presence of IR absorption at 1835 cm$^{-1}$ was characteristic of a β-lactone carbonyl stretching band and therefore strongly supports cyclization between C-4" and the hydroxyl at C-2". The lack of HMBC correlation between H-2" and C-1 also supported a β-lactone cyclization. The presence of the β-lactone was further confirmed by the instability of 1 in mild acidic conditions resulting in polymerization. The relative configuration at the C-2" and C-3" positions on the β-lactone moiety was determined from an analysis of the $^3J_{HH}$ values. A small $^3J_{H2"-H3"}$ of 3.8 Hz revealed that H-2" and H-3" have a trans configuration, thus the relative configuration of the ring was determined to be (2R*, 3S*).

The absolute configurations of the amino acids in cystargolide A were determined using Marfey's analysis. The peptides were hydrolyzed in HCl, derivatized using L-FDAA and compared to authentic derivatized amino acid standards using LC-HRMS. The derivatized hydrolysate of 1 gave peaks at 28.8 and 34.0 minutes, which corresponded to L-Ile (34.0 min) and L-Val (28.7 min). Mosher's method was attempted to determine the absolute configuration of the β-lactone moiety after hydrolysis of cystargolides with 1N NaOH. Unfortunately, both R and S Mosher's derivatives were not detected by LC-HRMS analysis which is most likely due to the instability of the β-lactone moiety leading to polymerization of 1 and 2. Cystargolide B (2) was isolated as a pale yellow powder, and HRESIMS supported a molecular formula of C$_{17}$H$_{28}$N$_2$O$_6$ (m/z 357.2021 [M+H]$^+$, Δ=0.2 ppm), which suggested the absence of one methylene group. Table 2 presents $^1$H and $^{13}$C NMR data for Cystargolide B (2). The NMR spectra of 2 closely resembled those of 1 while HSQC correlations revealed the absence of two signals, $\delta_H$ 1.43 (H$_2$-5$_a$) and $\delta_H$ 1.19 (H$_2$-5b), which are in agreement with valine replacing isoleucine. The interpretation of COSY, HMBC, and tandem mass spectrometry data further confirmed these observations and indicate the replacement of the isoleucine to a second valine residue. Marfey's analysis indicated that both valines possess an L-configuration and the $^3J_{BH}$ coupling constants similarly revealed a trans substituted β-lactone.

TABLE 1

$^1$H (600 MHz) and $^{13}$C (150 MHz) NMR data for 1 recorded in DMSO-d$_6$

| Position | $\delta_C$, type | $\delta_H$ (J in Hz) | $^1$H-$^1$H COSY | HMBC (H→C) | NOESY |
|---|---|---|---|---|---|
| 1 | 172.8, C | | | | |
| 2 | 56.4, CH | 4.16, dd (7.1, 7.1) | 3, NHa | 1, 3, 4, 5, 1' | 3, 4, NHa |
| 3 | 36.0, CH | 1.78, m | 2, 4, 5 | 1, 2, 4, 5, 6 | 2 |
| 4 | 15.3, CH$_3$ | 0.86, m | 3 | 3, 5 | |
| 5 | 24.5, CH$_2$ | 1.43, m | 3, 6 | 2, 3, 4, 6 | |
| | | 1.19, m | 3, 6 | 2, 3, 4, 6 | |
| 6 | 10.9, CH$_3$ | 0.82, m | 5 | 3, 5 | |
| NHa | | 8.12, d (8.0) | 2 | 1, 2, 3, 1' | 2, 5, 2', 3' |
| 1' | 170.5, C | | | | |
| 2' | 57.2, CH | 4.37, dd (8.0, 8.0) | 3', NHb | 1', 3', 4', 5', 1" | 3', NHa, NHb, 4' |
| 3' | 30.7, CH | 2.01, m | 2', 4', 5' | 1', 2', 4' | 2' |
| 4' | 18.8, CH$_3$ | 0.87, m | 3' | 2', 3', 5' | |
| 5' | 17.4, CH$_3$ | 0.81, m | 3' | 2', 3', 4' | |
| NHb | | 8.53, d (9.0) | 2' | 2', 3', 1", 2" | 2', 3', 2" |
| 1" | 167.3, C | | | | |
| 2" | 70.0, CH | 5.01, d (4.0) | 3" | 1", 3", 4", 5" | NHb, 3", 5", 6" |
| 3" | 62.6, CH | 3.50, dd (4.1, 8.1) | 2", 5" | 1", 2", 4", 5", 6", 7" | 5', 2", 5", 7" |
| 4" | 169.8, C | | | | |
| 5" | 26.4, CH | 2.11, m | 3", 6", 7" | 2", 3", 4", 6", 7" | 2", 3" |
| 6" | 19.0, CH$_3$ | 1.00, d (6.7) | 5" | 3", 5", 7" | |
| 7" | 19.2, CH$_3$ | 0.97, d (6.7) | 5" | 3", 5", 6" | |

TABLE 2

$^1$H (600 MHz) and $^{13}$C (150 MHz) NMR data for (2) DMSO-$d_6$

| Position | δC, type | δH (J, Hz) | $^1$H-$^1$H COSY | HMBC (H→C) | NOESY |
|---|---|---|---|---|---|
| 1 | 172.5, C | | | | |
| 2 | 57.2, CH | 4.12 dd (6.6, 6.6) | 3, NHa | 1, 3, 4, 1' | 4 |
| 3 | 29.4, CH | 2.06 m | 2, 4, 5 | 1, 2, 5 | |
| 4 | 17.7, CH$_3$ | 0.89 m | | 5 | |
| 5 | 18.8, CH$_3$ | 0.88 m | | 2, 3 | |
| NHa | | 8.11 d (8.1) | 2 | 1, 3, 1', 2' | 5, 2', 3' |
| 1' | 170.5, C | | | | |
| 2' | 57.2, CH | 4.38 t (7.7) | 3', NHb | 5, 3', 5', 1" | 3', NHa, NHb, 4' |
| 3' | 30.7, CH | 2.01 m | 2', 4', 5' | 5, 2', 4' | |
| 4' | 18.9, CH$_3$ | 0.86 m | 3' | 2', 3', 5' | |
| 5' | 17.6, CH$_3$ | 0.82 d (6.7) | 3' | 2', 3', 4' | |
| NHb | | 8.53 d (9.0) | 2' | 2', 3', 1", 2" | 2', 3', 2" |
| 1" | 167.0, C | | | | |
| 2" | 69.9, CH | 5.01 d (3.8) | 3" | 1", 3", 4", 5" | 3", 5", NHb, 6" |
| 3" | 62.5, CH | 3.51 dd (3.9, 8.1) | 2", 5" | 1", 2", 4", 5", 6", 7" | 2", 5", 6" |
| 4" | 169.7, C | | | | |
| 5" | 26.4, CH | 2.12 m | 3", 6", 7" | 2", 3", 4", 6", 7" | 3" |
| 6" | 19.2, CH$_3$ | 1.00 d (6.7) | 5" | 3", 4", 5" | |
| 7" | 19.3, CH$_3$ | 0.97 d (6.5) | 5" | 3", 4", 5" | |

FIGS. 4-24 show HRMS, NMR, IR spectra, and Marfey's analysis chromatograms relating to Cystargolides A (1) and B (2), as shown in Table 3.

TABLE 3

Characterization data for Cystargolides A (1) and B (2)

| FIG. No. | Data Shown | Subject Compound |
|---|---|---|
| 4 | +ESIHRMS | Cystargolide A |
| 5 | MS$^3$ Spectrum | Cystargolide A |
| 6 | $^1$H NMR Spectrum | Cystargolide A |
| 7 | $^{13}$C NMR Spectrum | Cystargolide A |
| 8 | COSY NMR Spectrum | Cystargolide A |
| 9 | NOESY NMR Spectrum | Cystargolide A |
| 10 | HSQC NMR Spectrum | Cystargolide A |
| 11 | HMBC NMR Spectrum | Cystargolide A |
| 12 | Marfey's analysis | Cystargolide A |
| 13 | Marfey's analysis | Amino acid standards |
| 14 | IR Spectrum | Cystargolide A |
| 15 | +ESIHRMS | Cystargolide B |
| 16 | MS$^3$ Spectrum | Cystargolide B |
| 17 | $^1$H NMR Spectrum | Cystargolide B |
| 18 | $^{13}$C NMR Spectrum | Cystargolide B |
| 19 | COSY NMR Spectrum | Cystargolide B |
| 20 | NOESY NMR Spectrum | Cystargolide B |
| 21 | HSQC NMR Spectrum | Cystargolide B |
| 22 | HMBC NMR Spectrum | Cystargolide B |
| 23 | Marfey's analysis | Cystargolide B |
| 24 | IR Spectrum | Cystargolide B |

Figure 3:
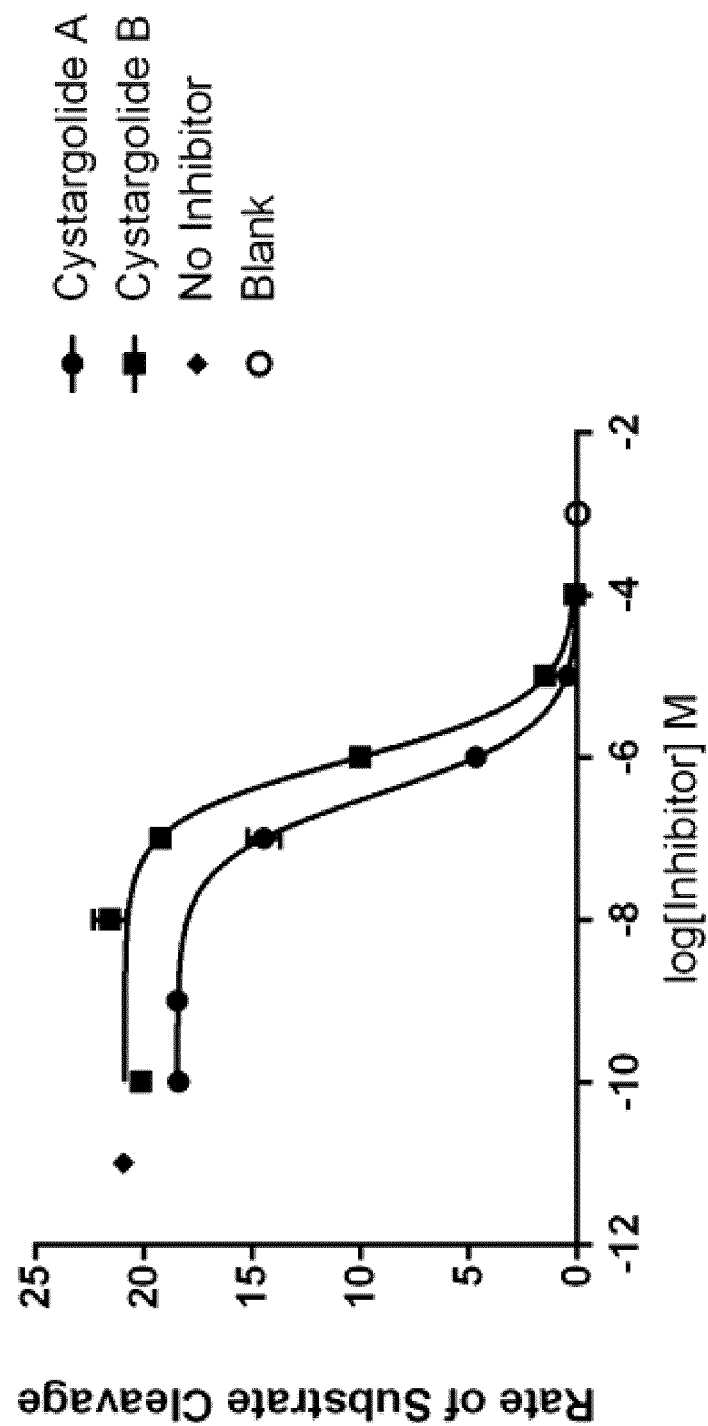
FIG. 3 illustrates a dose-response curve showing the effects on the rate of Suc-LLVY-AMC cleavage by human 20S proteasome (AFU/s Ex 360 nm, Em 460 nm) in the presence of increasing concentrations of cystargolides A and B. No inhibitor and blank values show maximal and minimal rates of substrate cleavage.
Figure 4:
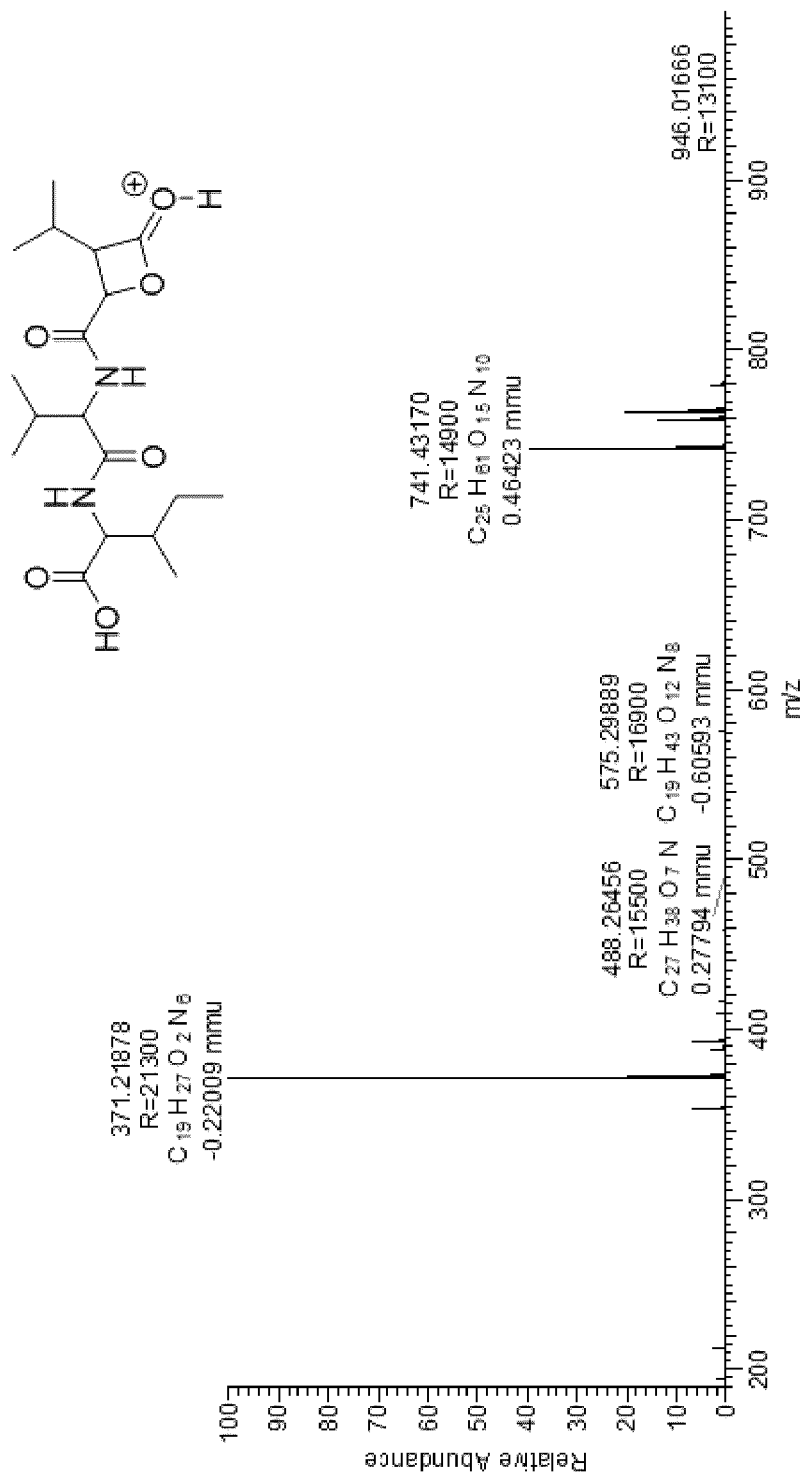
FIG. 4 shows the +ESIHRMS of Cystargolide A (1)
Figure 5:
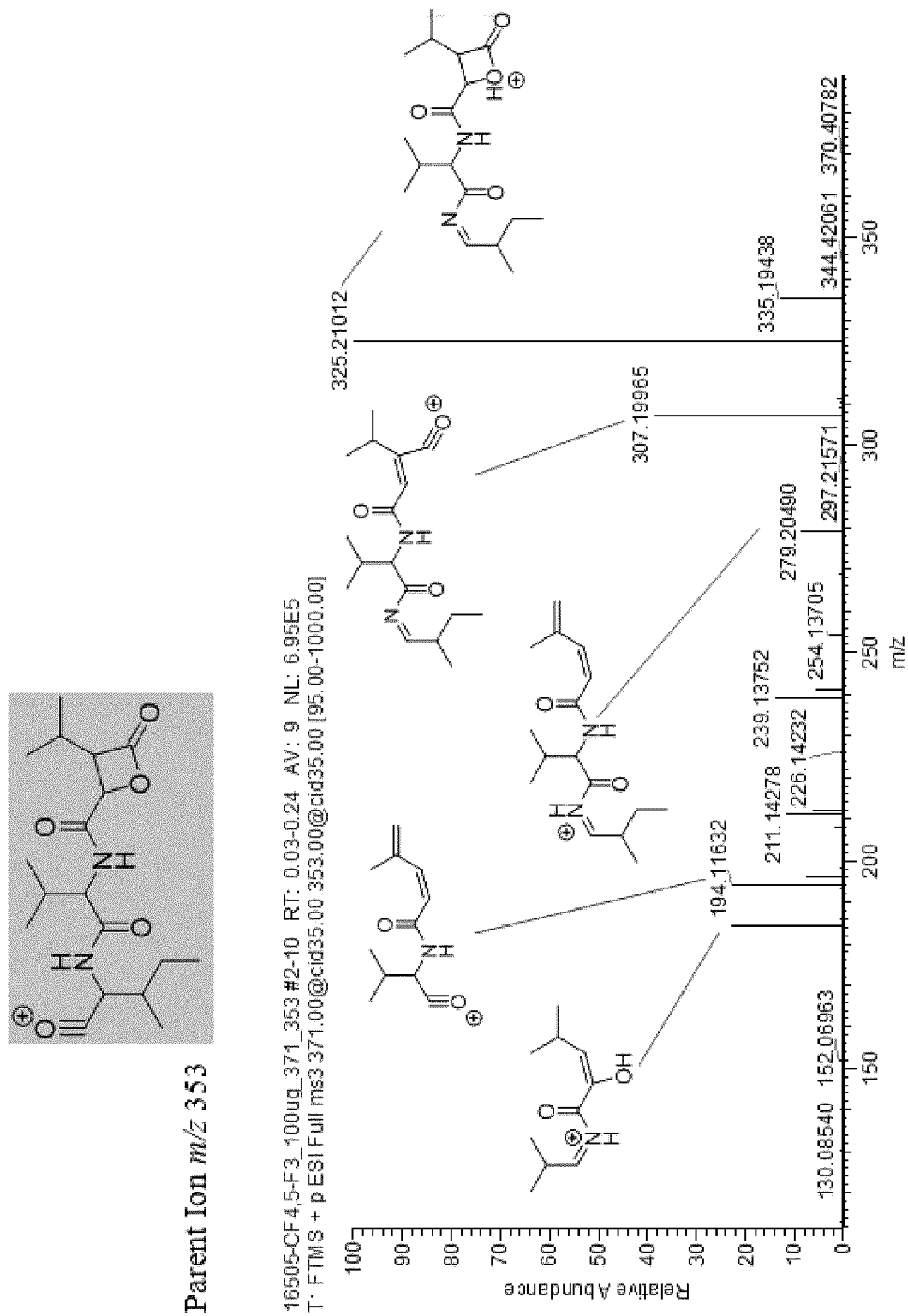
FIG. 5 shows the $MS^3$ spectrum of Cystargolide A (1)
Figure 6:
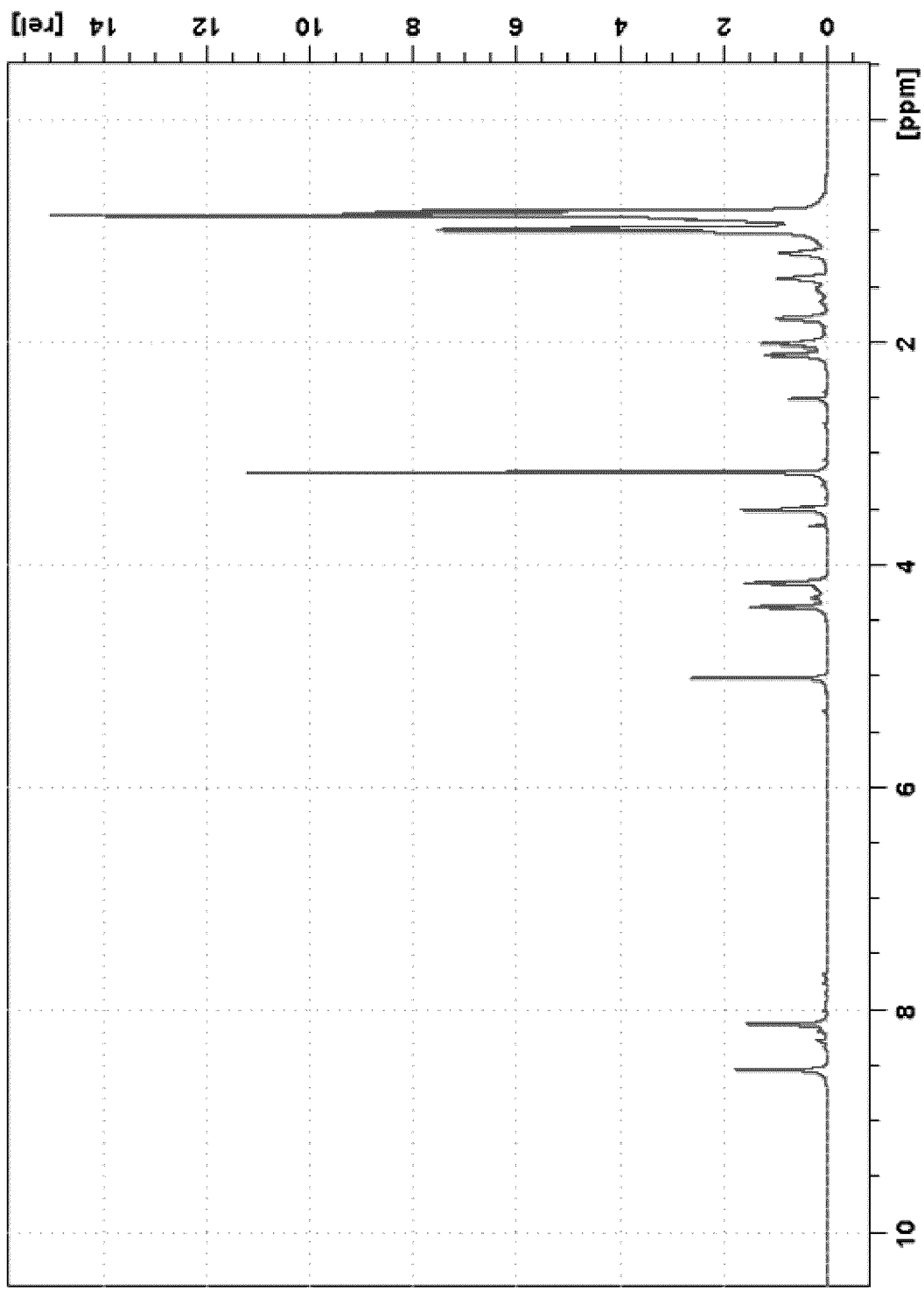
FIG. 6 shows the $^1H$ NMR (600 MHz, DMSO-$d_6$) spectrum of Cystargolide A (1)
Figure 7:
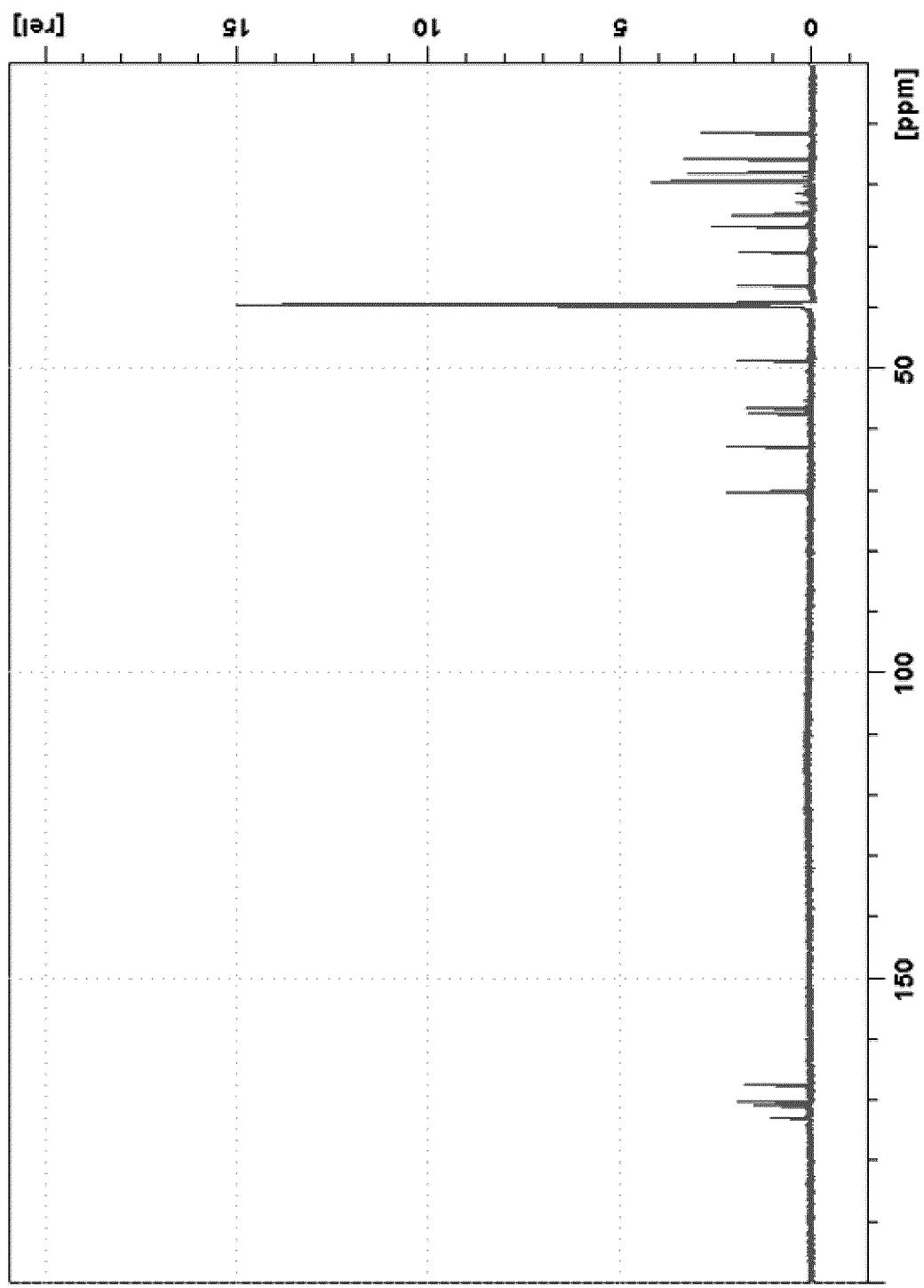
FIG. 7 shows the $^{13}C$ NMR (150 MHz, DMSO-$d_6$) spectrum of Cystargolide A (1)
Figure 8:
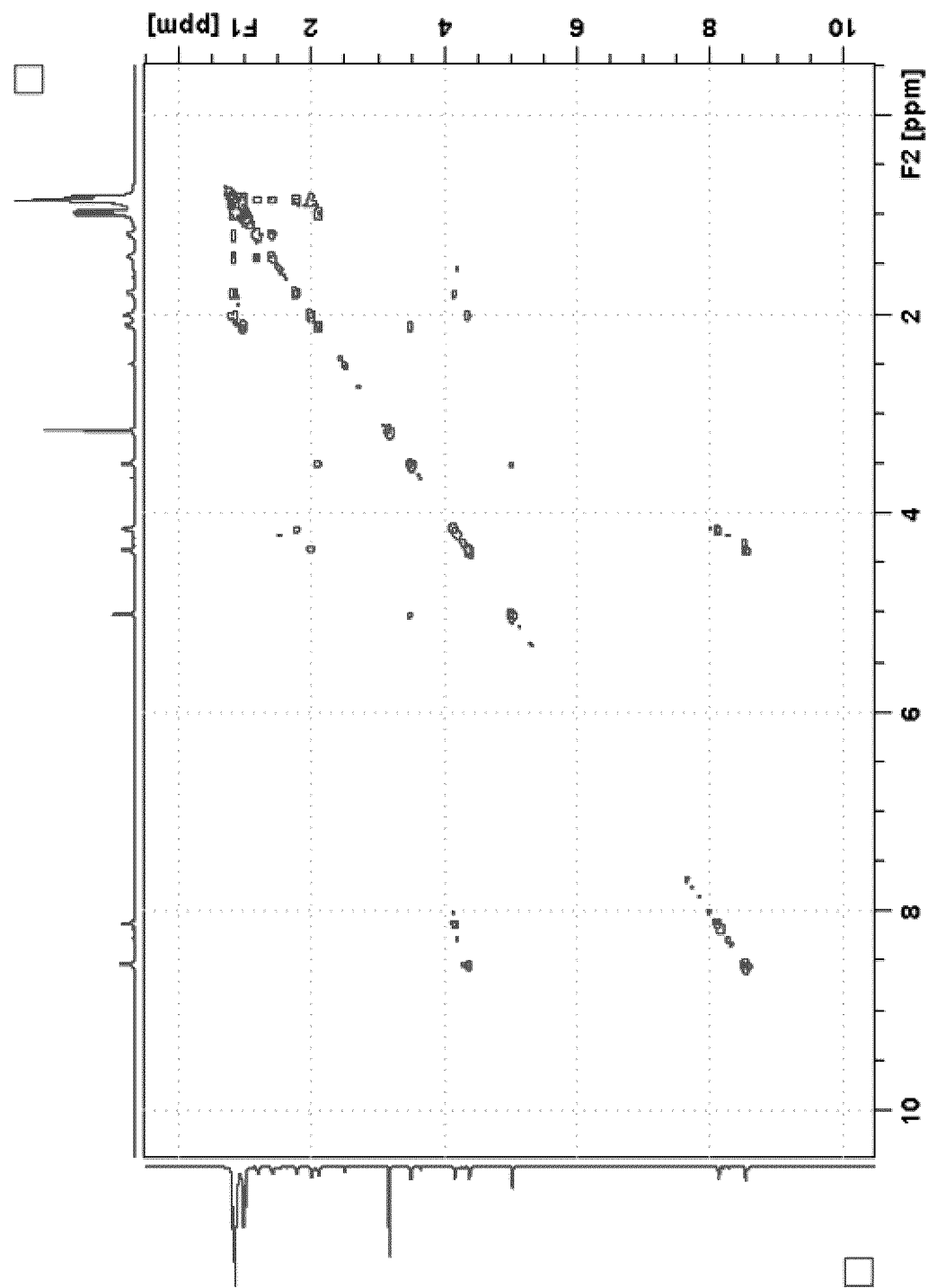
FIG. 8 shows the COSY ($^1H$, 600 MHz, DMSO-$d_6$) NMR spectrum of Cystargolide A (1)
Figure 9:
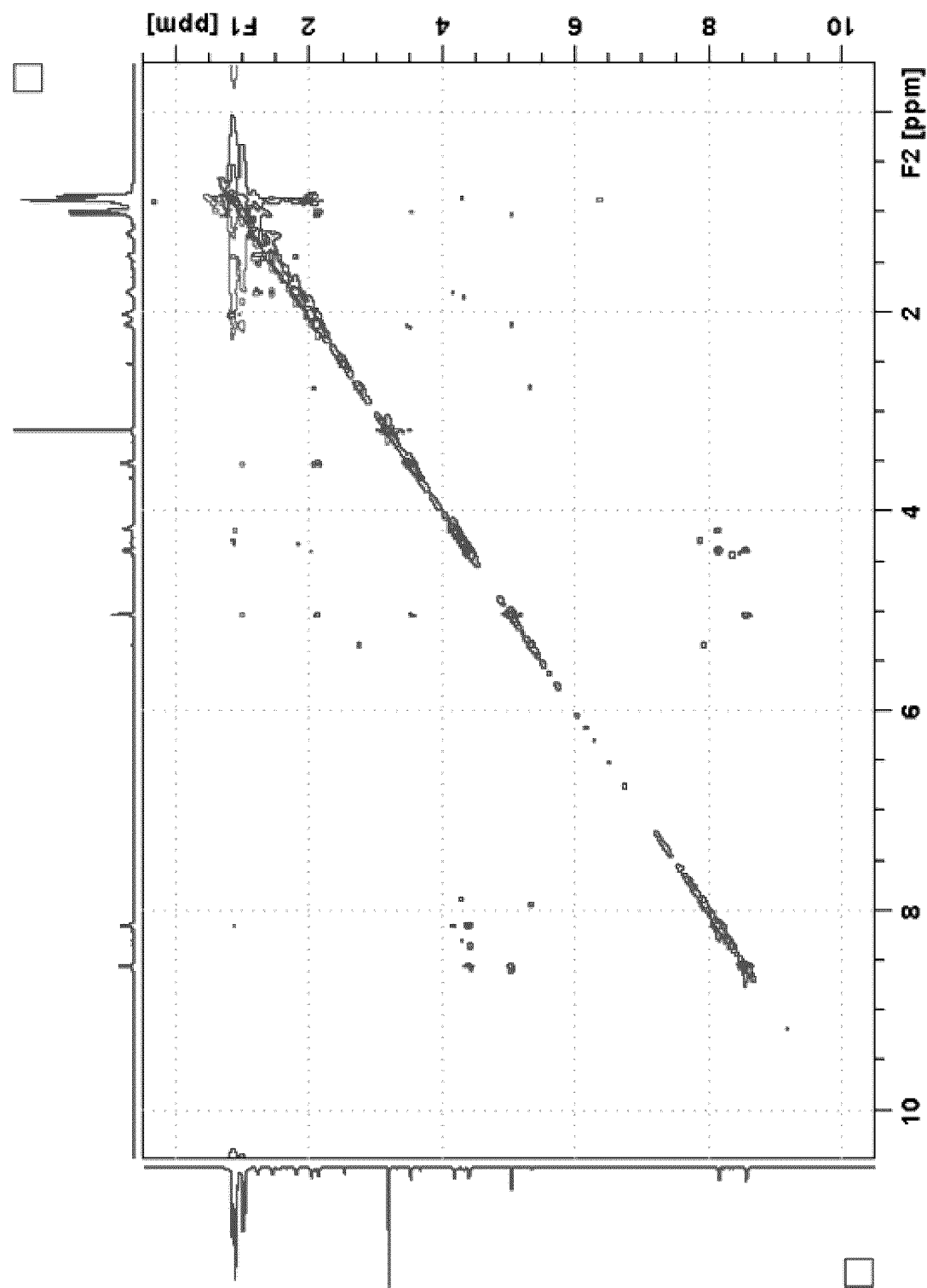
FIG. 9 shows the NOESY (1H, 600 MHz, DMSO-$d_6$) NMR spectrum of Cystargolide A (1)
Figure 10:
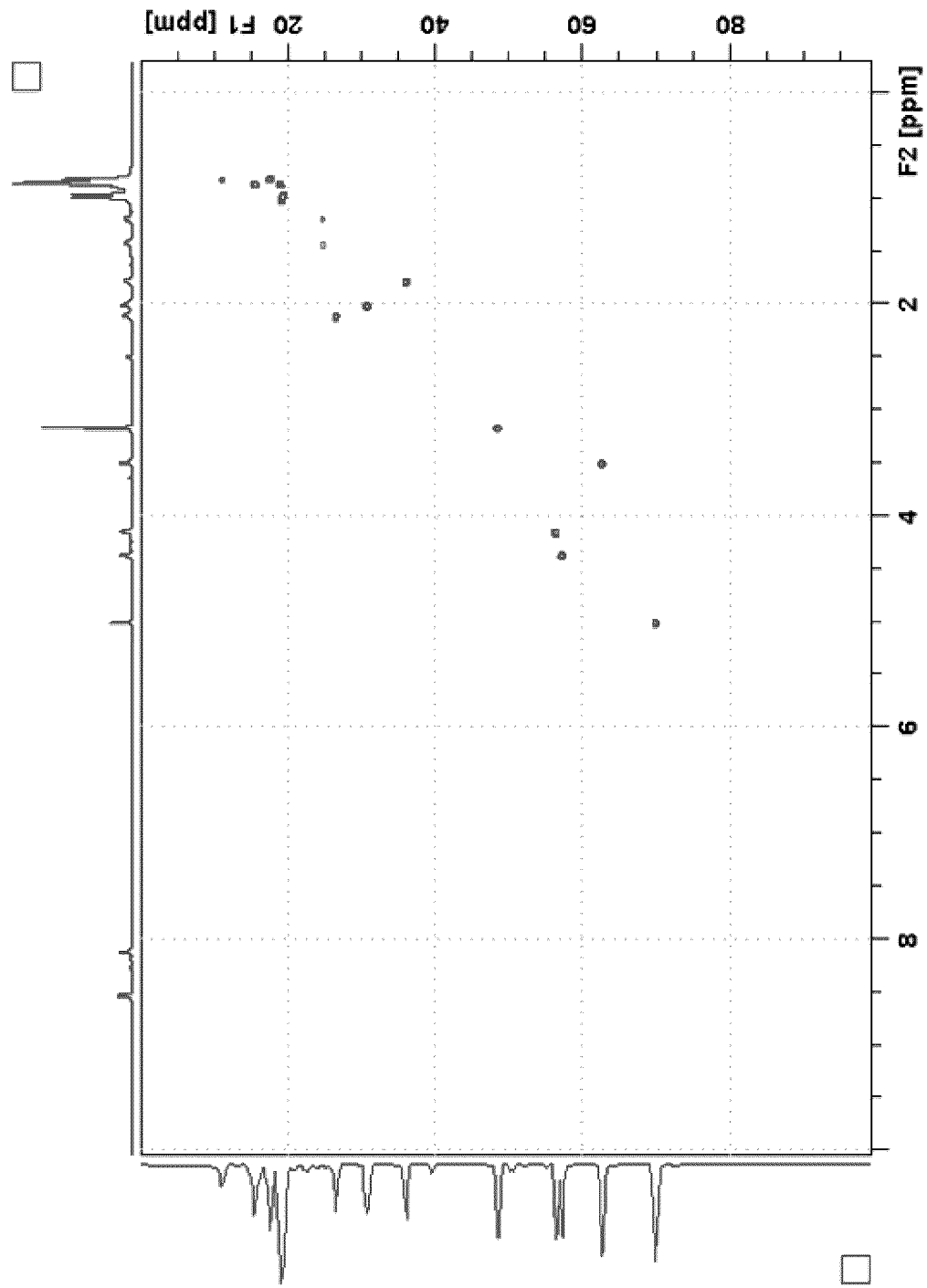
FIG. 10 shows the HSQC NMR ($^1H$ 600 MHz, $^{13}C$ 150 MHz, DMSO-$d_6$) spectrum of Cystargolide A (1)
Figure 11:
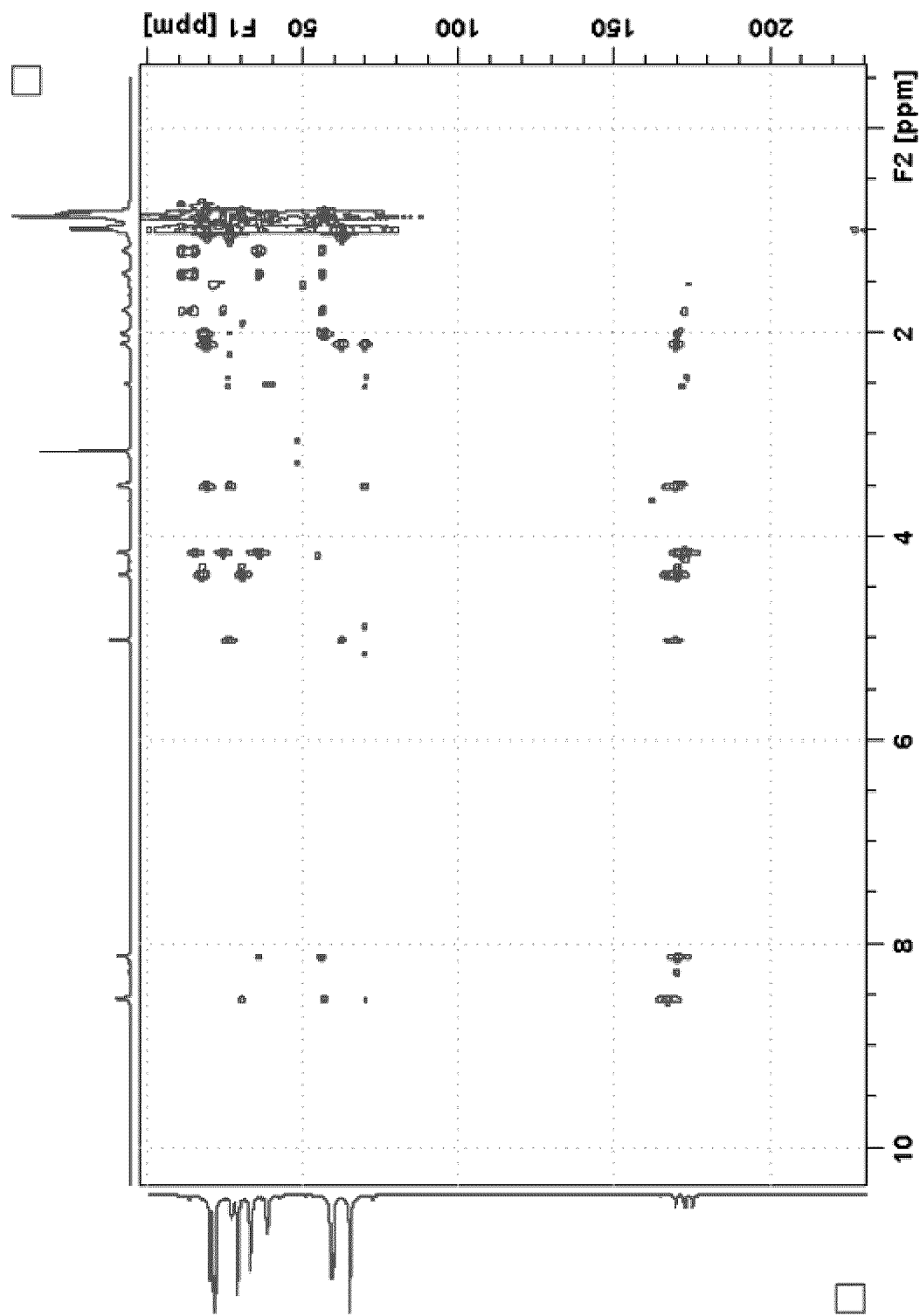
FIG. 11 shows the HMBC NMR ($^1H$ 600 MHz, $^{13}C$ 150 MHz, DMSO-$d_6$) spectrum of Cystargolide A (1)
Figure 12:
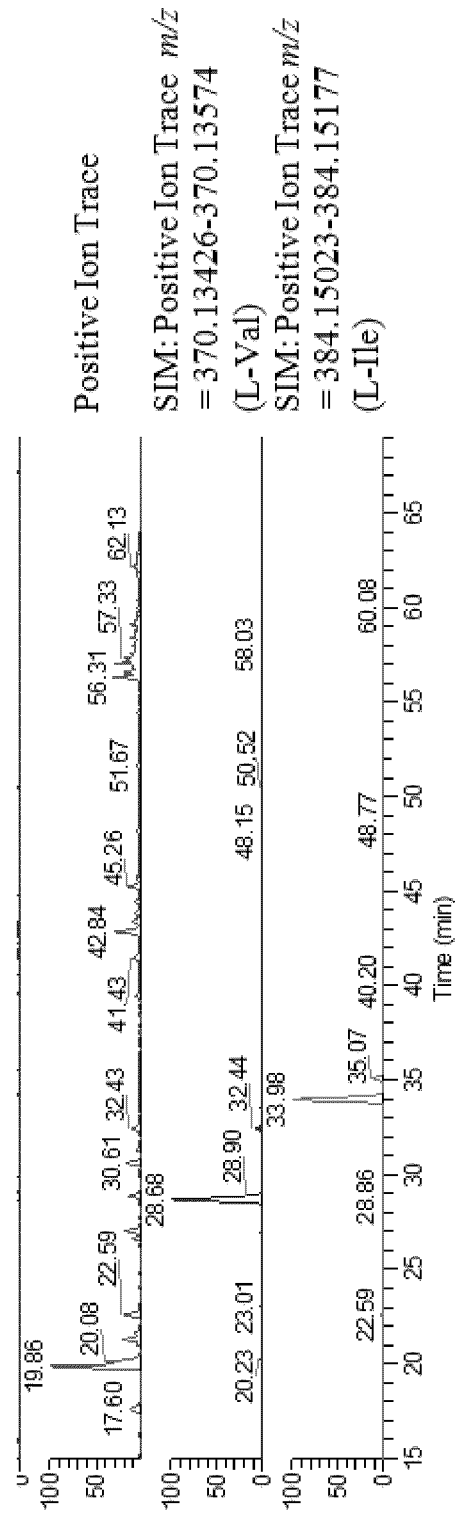
FIG. 12 shows the Marfey's (L-FDAA Dervatized) of Cystargolide A (1) hydrolsate via LC-HRMS analysis.
Figure 13:
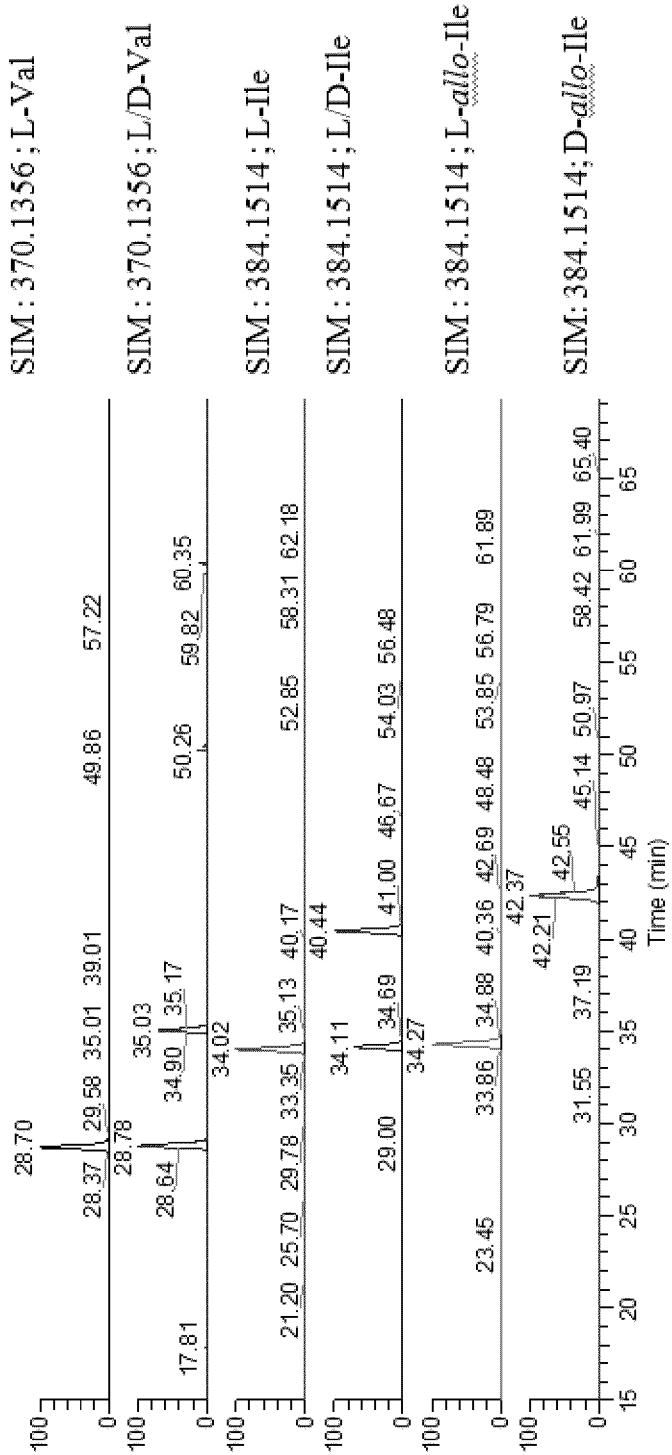
FIG. 13 shows the Marfey's (L-FDAA Derivatized) amino acid standards analysis.
Figure 14:
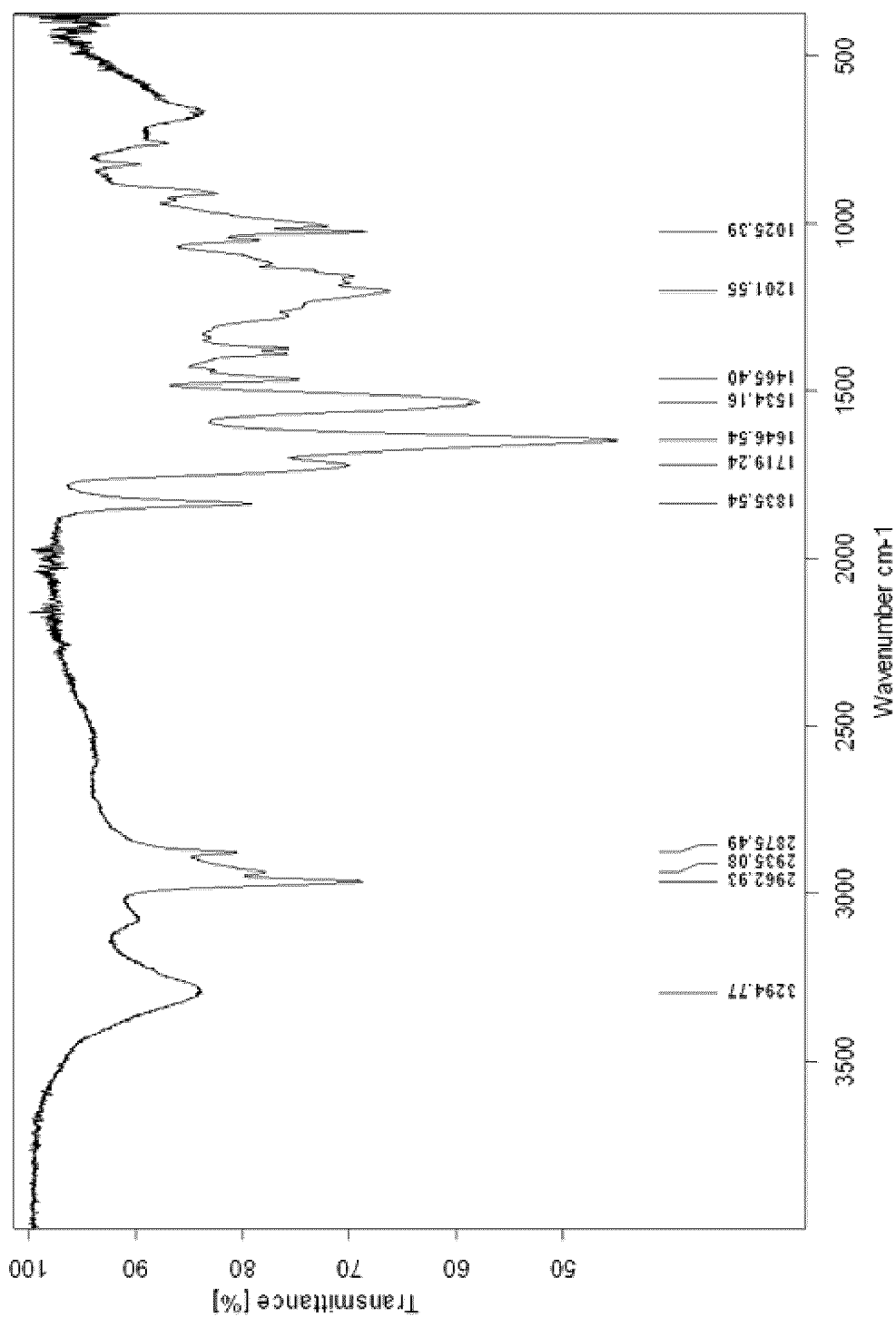
FIG. 14 shows the IR spectrum of Cystargolide A (1) (MeOH, film)
Figure 15:
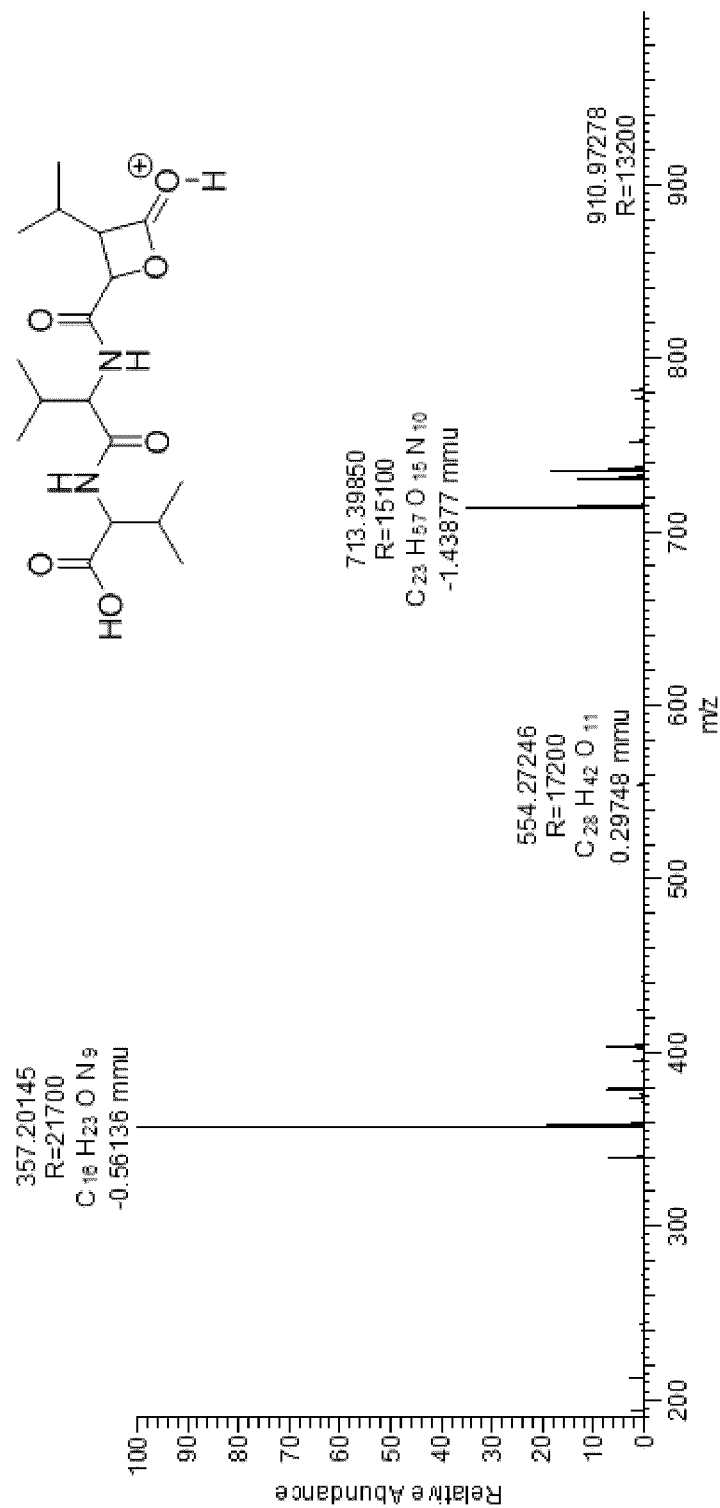
FIG. 15 shows the +ESIHRMS of Cystargolide B (2)
Figure 16:
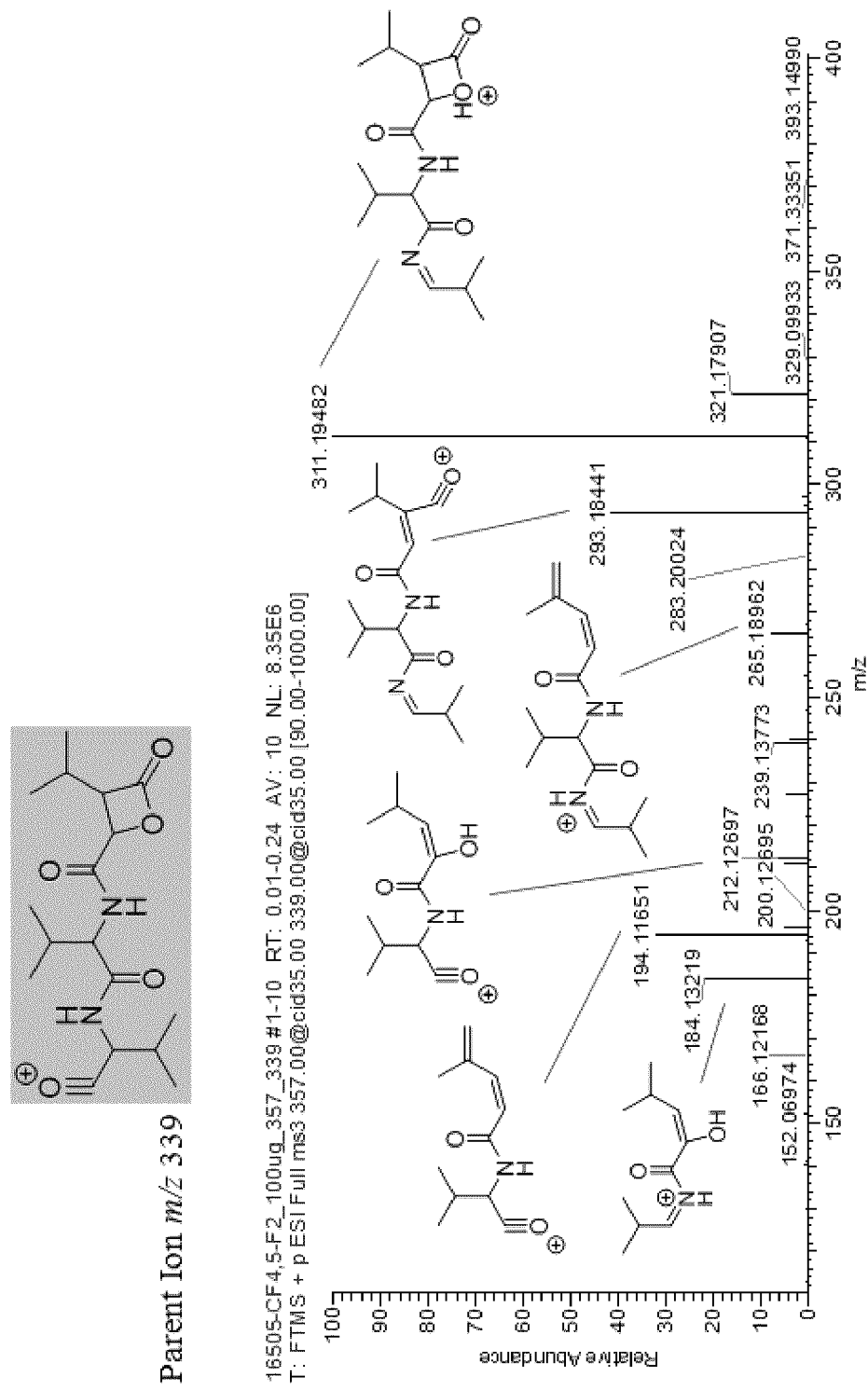
FIG. 16 shows the $MS^3$ spectrum of Cystargolide B (2)
Figure 17:
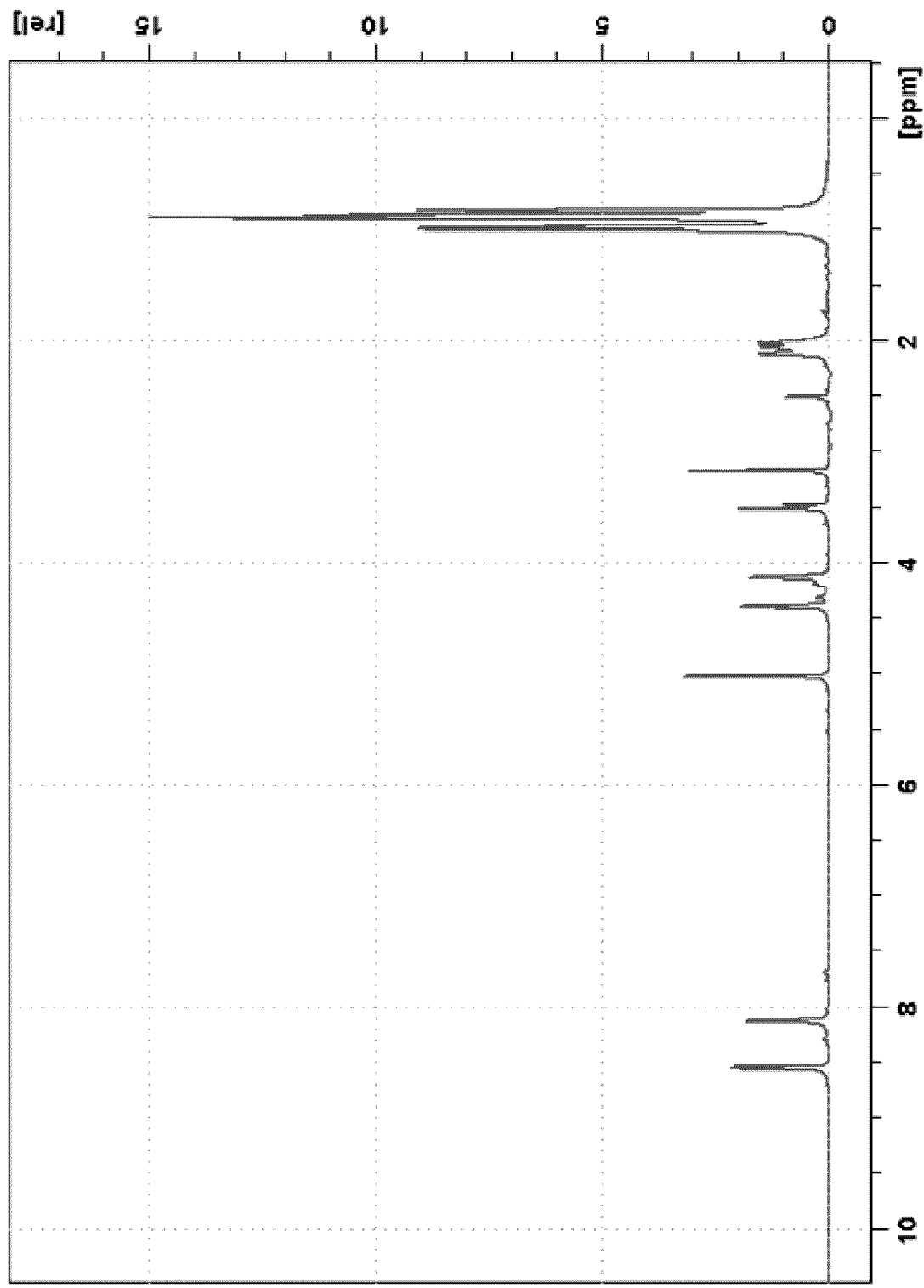
FIG. 17 shows the $^1HNMR$ (600 MHz, DMSO-$d_6$) spectrum of Cystargolide B (2)
Figure 18:
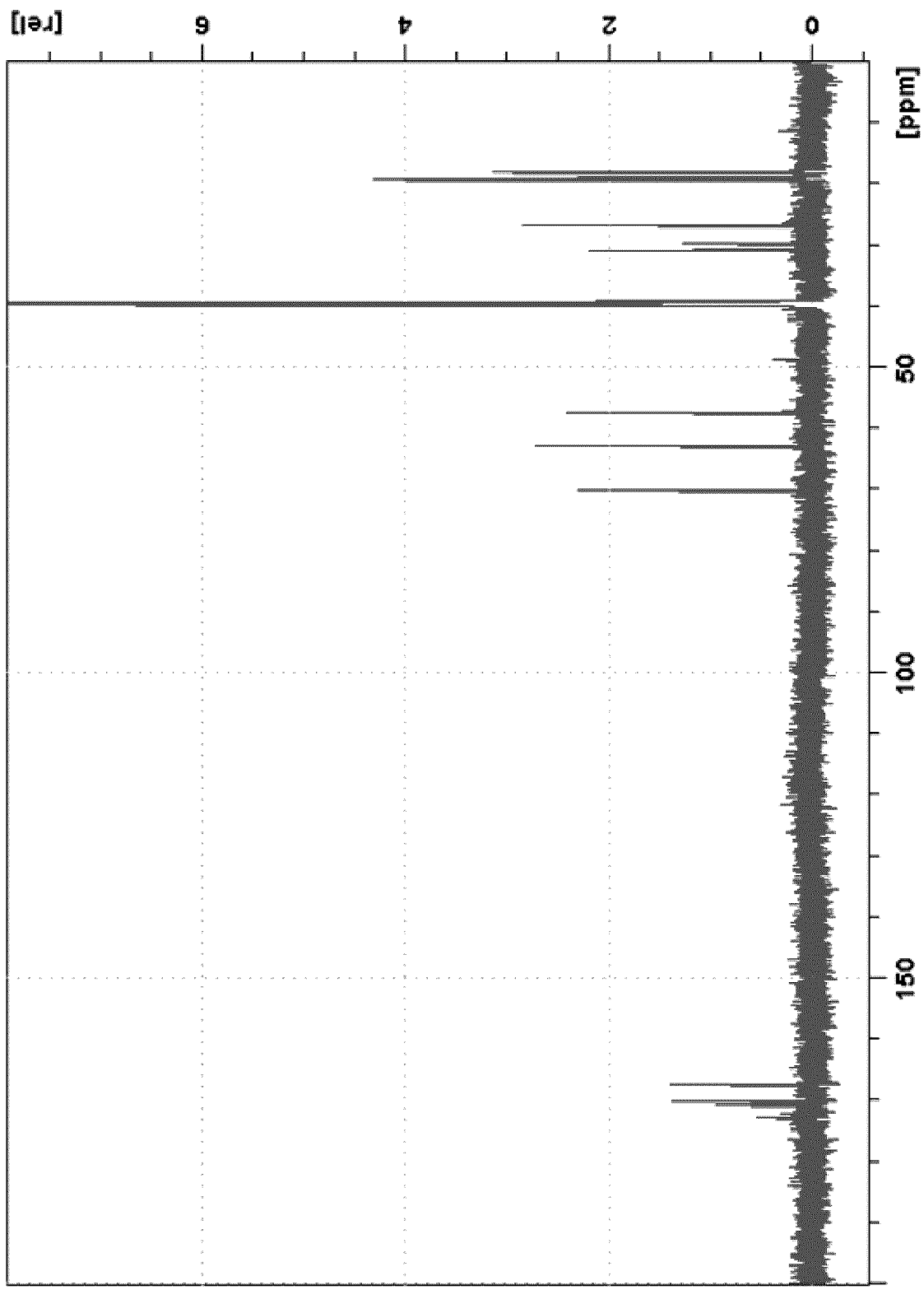
FIG. 18 shows the $^{13}C$ NMR (150 MHz, DMSO-$d_6$) spectrum of Cystargolide B (2)
Figure 19:
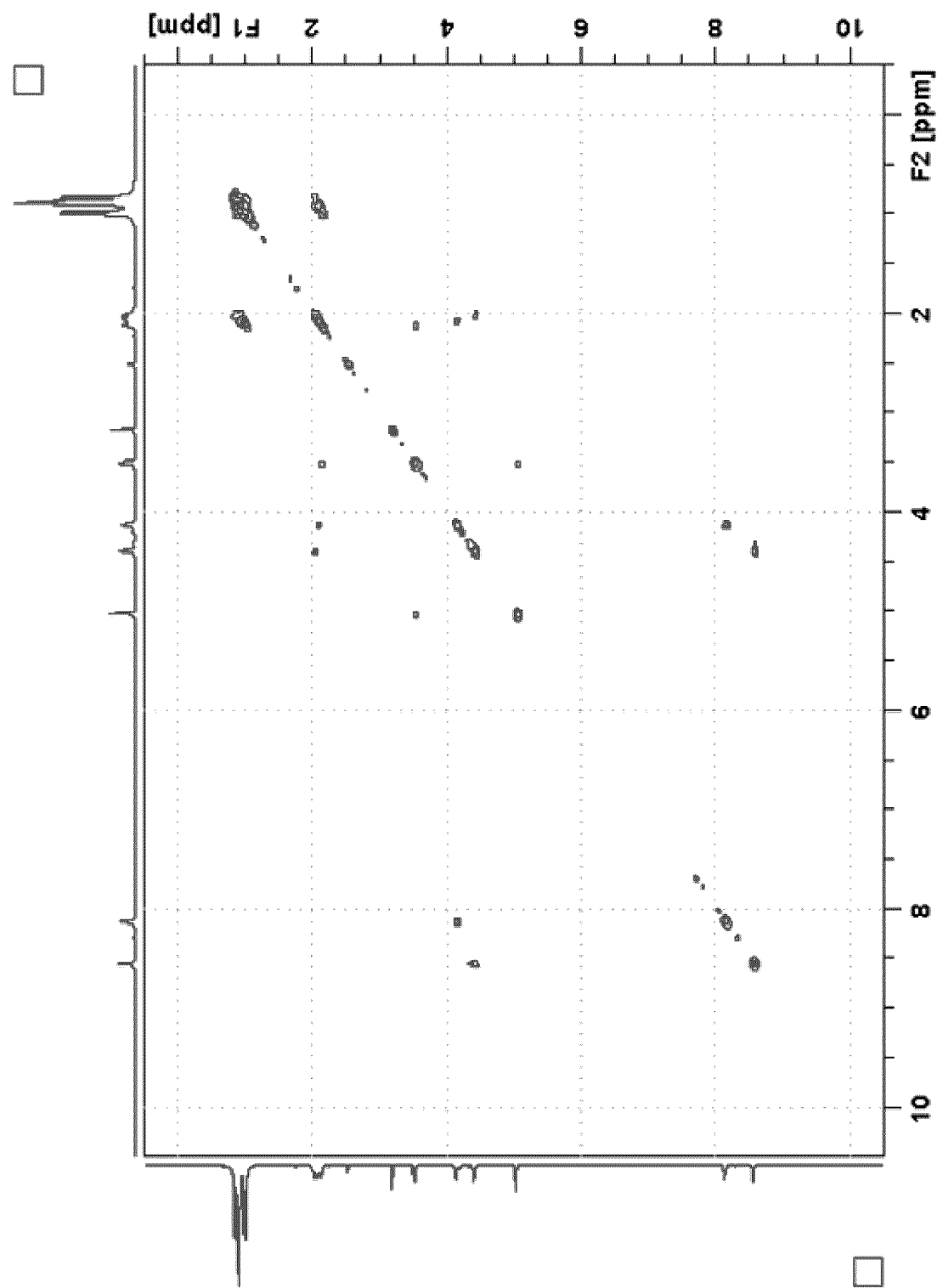
FIG. 19 shows the COSY NMR ($^1H$, 600 MHz, DMSO-$d_6$) spectrum of Cystargolide B (2)
Figure 20:
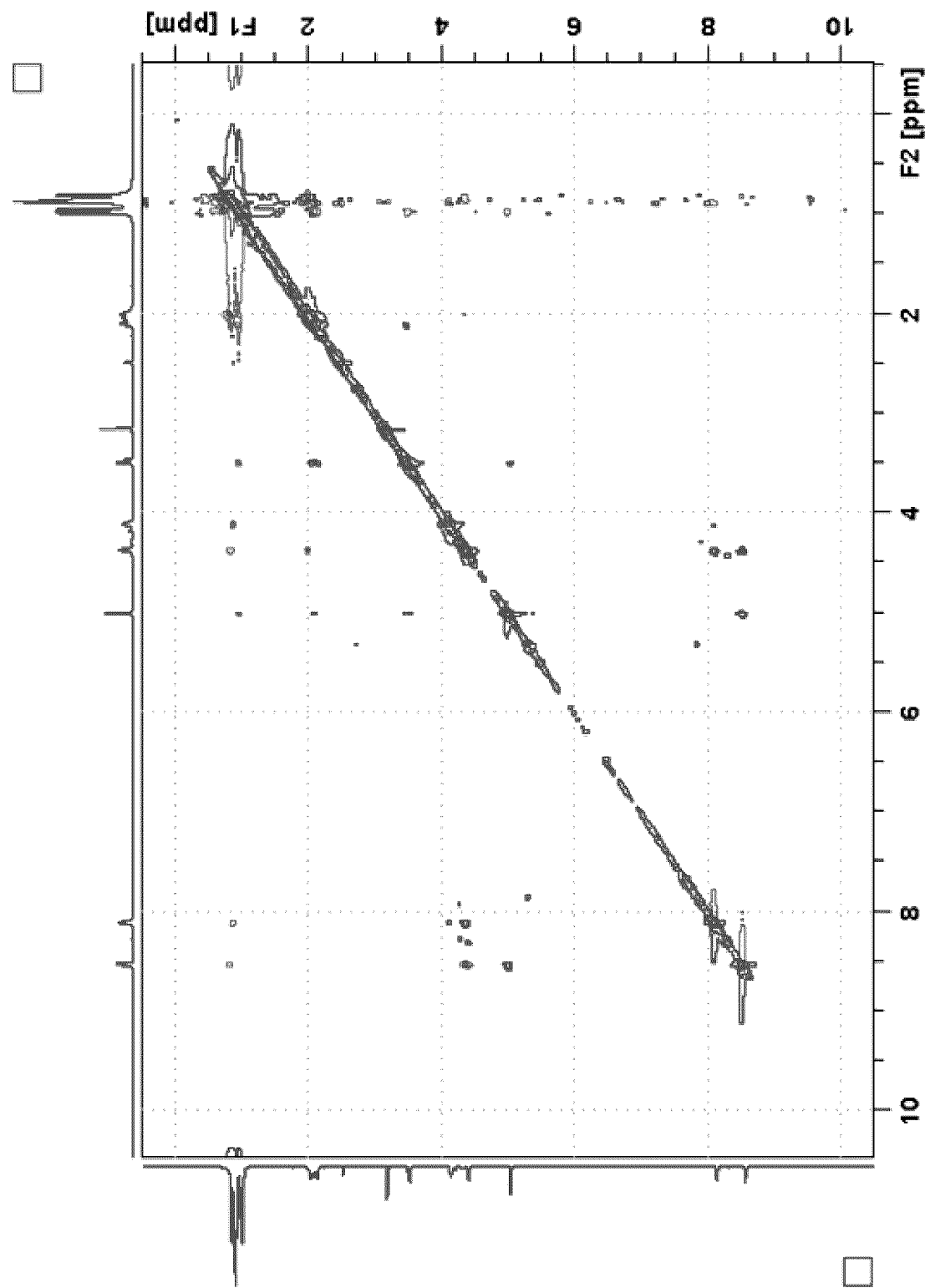
FIG. 20 shows the NOESY NMR (1H, 600 MHz, DMSO-$d_6$) spectrum of Cystargolide B (2)
Figure 21:
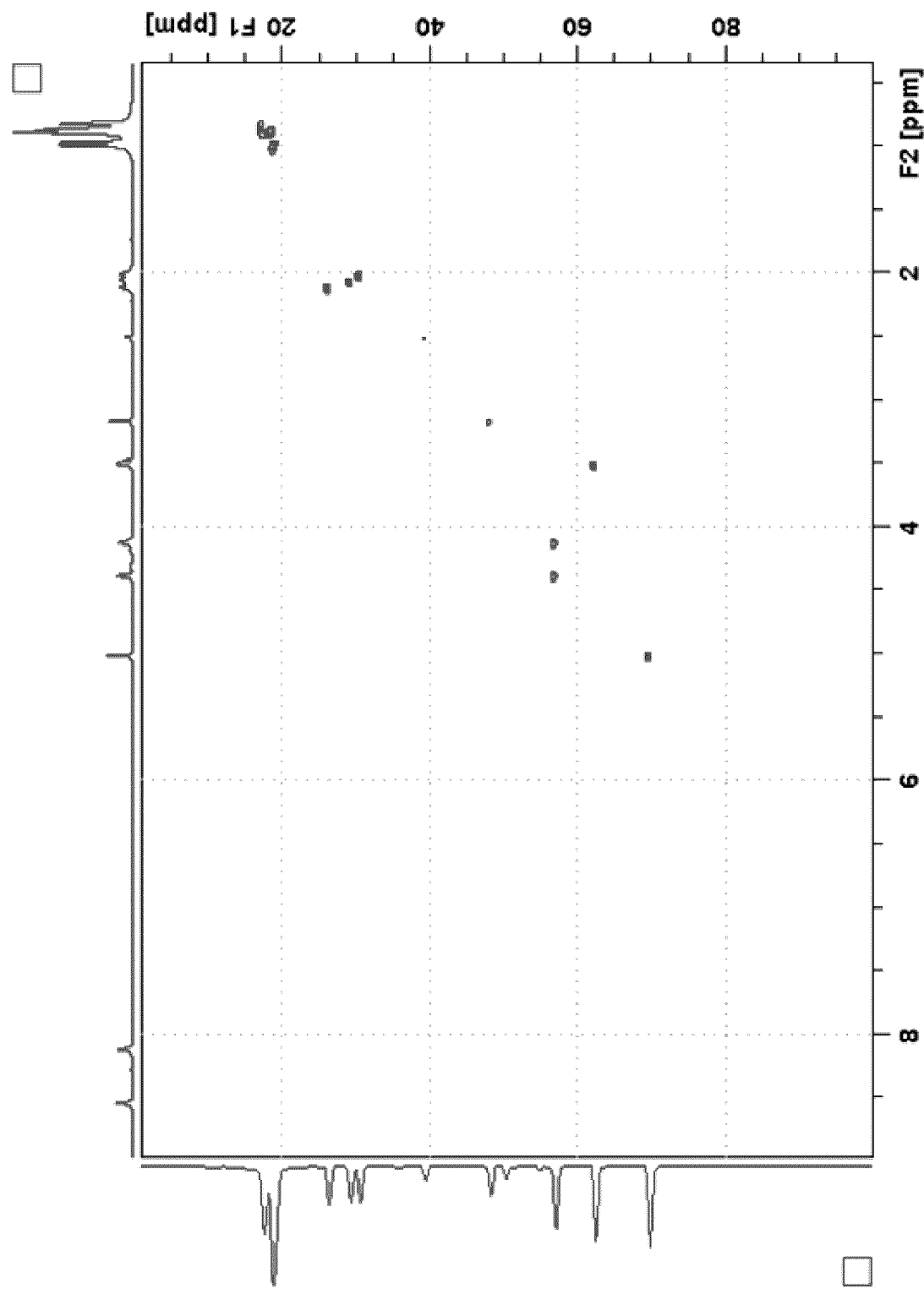
FIG. 21 shows the HSQC NMR ($^1H$ 600 MHz, $^{13}C$ 150 MHz, DMSO-$d_6$) spectrum of Cystargolide B (2)
Figure 22:
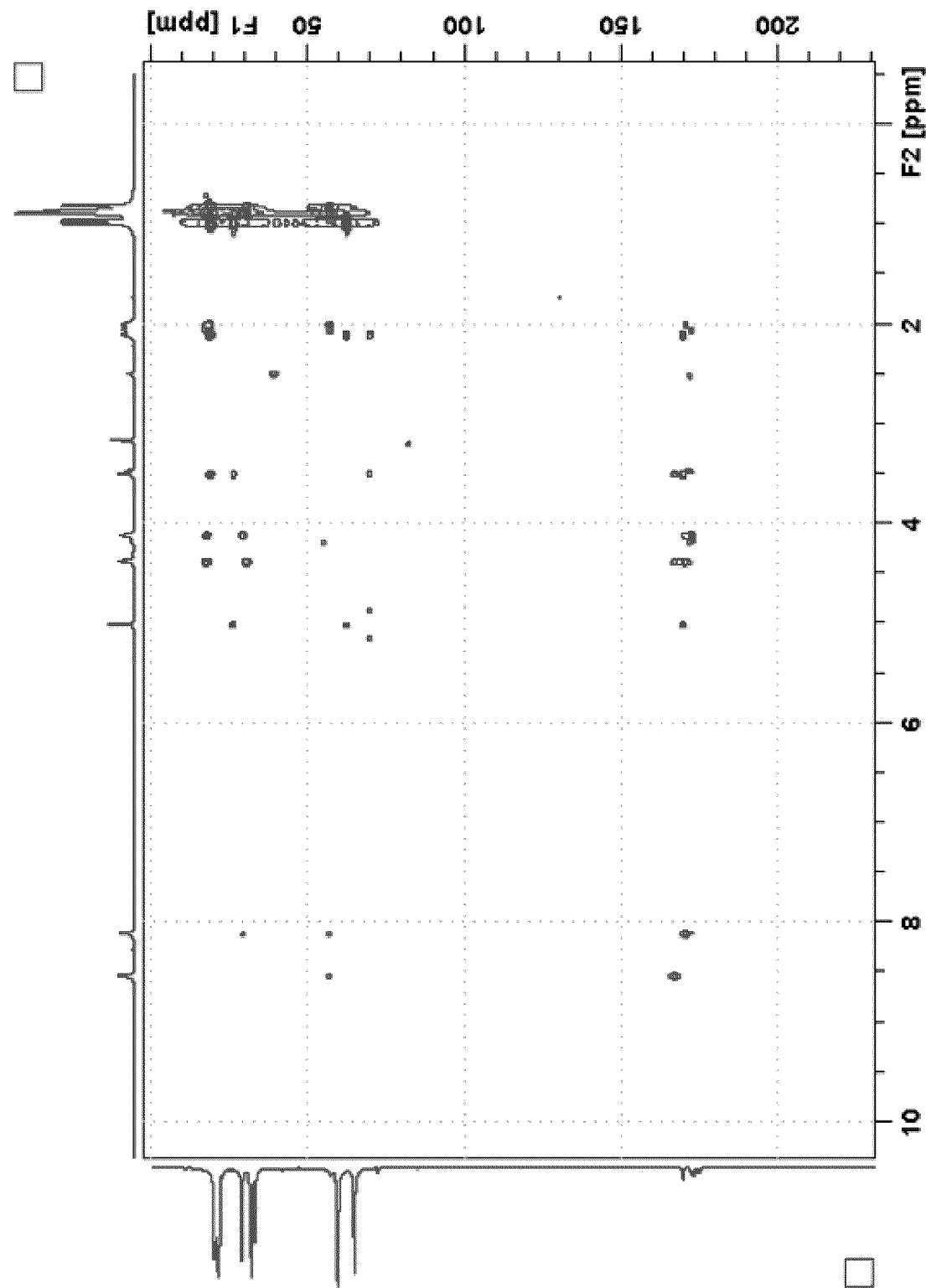
FIG. 22 shows the HMBC NMR CH 600 MHz, $^{13}C$ 150 MHz, DMSO-$d_6$) spectrum of Cystargolide B (2)
Figure 23:
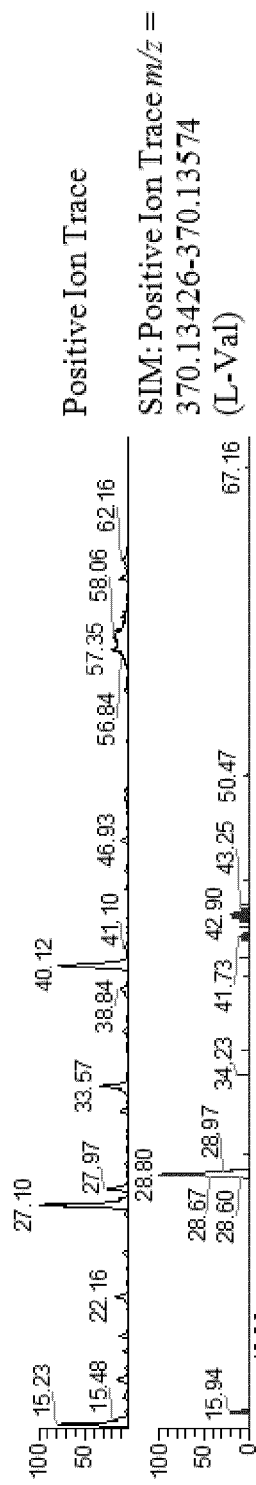
FIG. 23 shows the Marfey's (L-FDAA Derivatized) of Cystargolide B (2) hydrolysate via LC-HRMS analysis.
Figure 24:
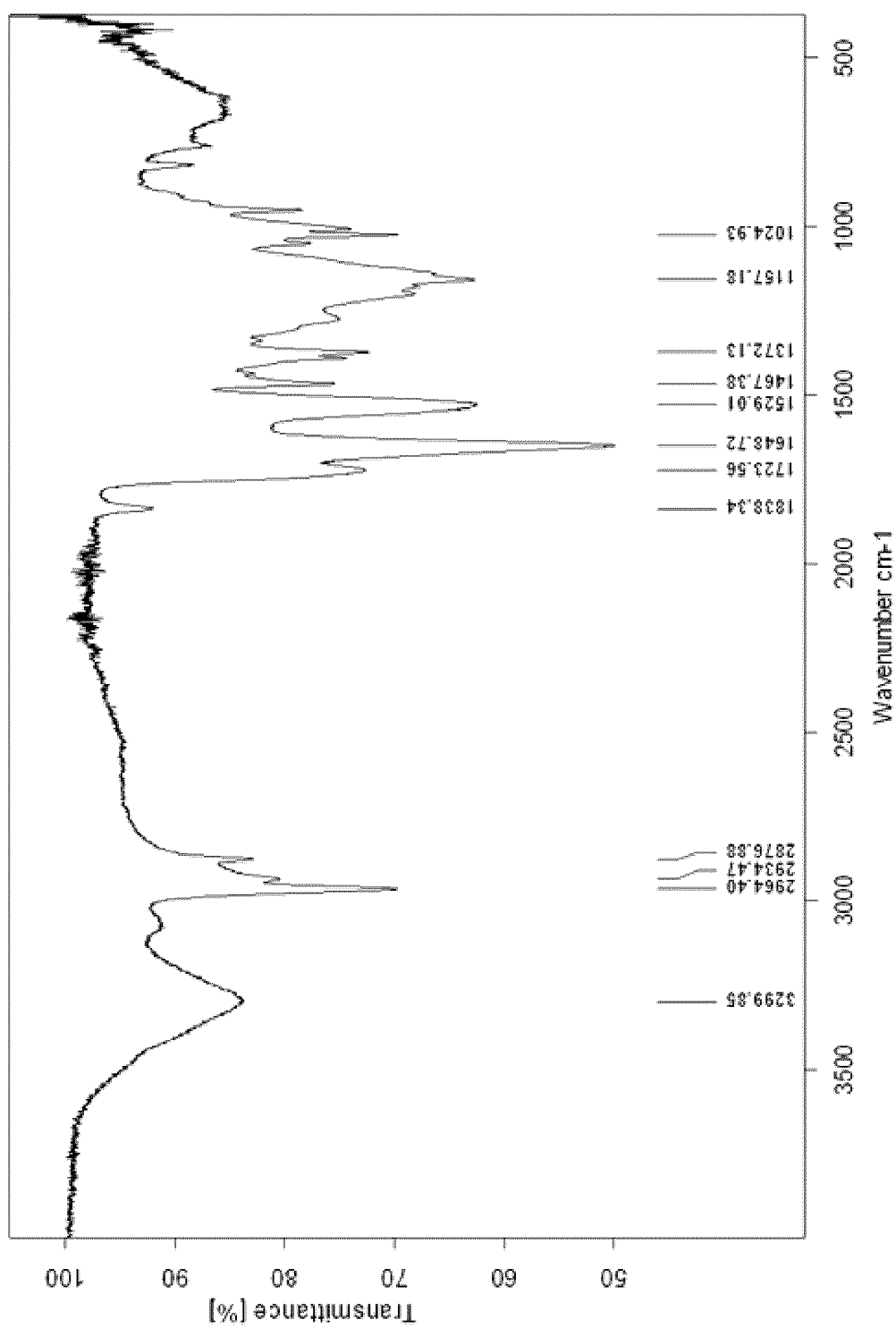
FIG. 24 shows the IR spectrum of Cystargolide B (2) (MeOH, film).

20S Proteasome Inhibition:

The presence of a β-lactone ring in the structures of 1 and 2 suggested that these natural products may be proteasome inhibitors, and so they were evaluated for their ability to inhibit human 20S proteasome in an enzyme assay. Varying concentrations of 1 and 2 were incubated with purified human 20S proteasome. To determine the chymotrypsin-like activity, the fluorogenic substrate Suc-LLVY-AMC was added and fluorescence was recorded to measure the rate of enzyme activity. A dose-response curve was used to calculate IC$_{50}$ values (see FIG. 3), which were determined to be 0.36 μM±0.017 and 0.93 μM±0.032 for 1 and 2 respectively.

Cystargolide A (1) was observed to be a more potent inhibitor than 2, suggesting that the additional methylene results in a small change to the bulkiness of the peptide side chain that increases the interaction with the 20S proteasome. The ability of 1 and 2 to inhibit chymotrypsin-like activity of the proteasome is consistent with results obtained using the natural products belactosins A and C. The β-lactone containing belactosins, A and C, inhibit chymotrypsin-like activity of the rabbit 20S proteasome both with an IC$_{50}$ value of 0.21 μM. This is similar to the value observed for 1, and slightly more potent than 2. Several medicinal chemistry and structure activity relationship studies of the belactosins have resulted in synthetic analogs and hybrids with increased potency and cell permeability resulting in improved lead compounds for the development of antiproliferative agents.

Experimental Procedures

General Experimental Procedures.

Optical rotations were measured on a Rudolph Autopol III polarimeter using a 50 mm microcell (1 mL). Infrared spectra were recorded using attenuated total reflectance, with samples deposited as a thin film on a Bruker Alpha FT-IR spectrometer. NMR spectra were obtained on a 600 MHz Bruker Avance III spectrometer equipped with a 1.7 mm inverse probe. Chemical shifts (δ) are reported in ppm and were referenced to the DMSO-d$_6$ residual peaks at δ$_H$ 2.50 ppm and δ$_C$ 39.51 ppm and coupling constants (J) are reported in Hz with the abbreviations (s) singlet, (d) doublet, (t) triplet, (q) quartet, (m) multiplet. LC-HRMS data were recorded on Accela Thermo equipment with hyphenated MS-ELSD-UV detection: Thermo LTQ Exactive fitted with ESI source, PDA, and LT-ELSD Sedex 80. High-resolution mass spectra were measured on a Thermo Orbitrap Velos mass spectrometer. MS/MS analysis was conducted in negative mode by direct infusion of cystargolide A and B at a rate of 2 μL/min using an ESI source and collision-induced dissociation (CID) energy of 35 eV. HPLC purifications were carried out on a Thermo Surveyor coupled with an evaporative light-scattering detector Sedex 55. L-valine, L/D-valine, L-isoleucine, L/D isoleucine, L-allo-isoleucine and D-allo-isoleucine were purchased from Sigma Aldrich (St. Louis Mo., USA).

Small Scale Fermentations and Statistic Analysis.

*Kitasatospora cystarginea* was obtained from the agriculture research service culture collection (NRRL B-16505) along with eleven other organisms classified as *Kitasatospora* spp. in the collection. Two seed cultures of each organism were fermented in a seed medium containing 10 g glucose and 10 g yeast extract per liter for 48 hours, each at 200 rpm and 30° C. 10 mL of a lean production medium was then inoculated in triplicate with 750 µL of seed culture and fermented for 72 hours under the same conditions. Medium blanks were also included as negative controls. The cultures were then extracted twice with 10 mL ethyl acetate (EtOAc), and the organic fractions were combined and evaporated to dryness. 10 µL (0.5 mg/mL in MeOH) of the fermentation extracts were analyzed by LC-HRMS using a Thermo LTQ Exactive HPLC system with a Core Shell 100 Å $C_{18}$ column (Kinetex, 1.7 µm 50×2.1 mm). A linear solvent gradient from 95% $diH_2O$/0.1% formic acid (solvent A) and 5% acetonitrile/0.1% formic acid (solvent B) to 100% solvent B over 4.8 minutes followed by an isocratic elution at 100% solvent B for 3.2 minutes with a flow rate of 500 µL/min was used. Eluent was detected by ESI-MS monitoring m/z 190-2000 in positive mode, ELSD, and UV 200-600 nm. LC-HRMS profiles were analyzed using principal component analysis and cluster analysis as previously described with the omission of intensity standardization. In brief, mzMine 2 was used for peak picking of LC-HRMS profiles, set with an intensity threshold of 1E4, followed by deisotoping, bucketing alignment, artifact suppression and statistical analysis using The Unscrambler (Camo Software).

Extraction and Isolation.

Two seed cultures of *K. cystarginea* NRRL-B16505 were fermented as previously described for 48 hours each, at 200 rpm and 30° C. 3 L of the lean production medium (4×750 mL) was then fermented with a 6.6% inoculum from seed cultures, for 72 hours under the same conditions.[26] Each fermentation was extracted with 500 mL and then 300 mL of EtOAc, which were then partitioned twice with equal volume of $diH_2O$. After evaporation, the combined extract was dissolved in 10 mL of 80% aqueous acetonitrile and partitioned with an equal volume of hexanes. The acetonitrile fraction was separated by reverse phase flash chromatography using CombiFlash Rf (Teledyne ISCO) with a 15.5 g $C_{18}$ column (High Performance GOLD, RediSep Rf), and eluted with a linear gradient from 50:50 $diH2O$:MeOH to 100% MeOH over 15 minutes followed by 100% MeOH for 5 minutes. A flow rate of 30 mL/min was used and eluent was detected by UV (214 nm). A mixture of 1 and 2 eluted at 6.0-8.5 minutes.

Cystargolides were purified using a Luna 110 Å phenyl hexyl column (5 µm, 250×10.00 mm, Phenomenex). $diH_2O$/0.1% formic acid (solvent A) and methanol/0.1% formic acid (solvent B) were used with a flow rate of 3 mL/min. The mixture was separated using a linear gradient increasing from 50% solvent B to 80% solvent B over 17 minutes, followed by a linear increase to 100% solvent B over 2 minutes and 100% solvent B for 12 minutes. 1 and 2 eluted at 10.2 and 12.1 minutes respectively, which were detected by ELSD and UV (220 and 254 nm).

Structure Elucidation.

Cystargolide A (1) Pale yellow power; $[\alpha]^{25}_D$ −18° (c=0.29, MeOH); IR $v_{max}$ 3294, 2962, 1835, 1719, 1646, 1534, 1465, 1201, 1025 $cm^{-1}$; $^1H$ and $^{13}C$ NMR see Table 1; (+) HRESIMS m/z 371.2177 $[M+H]^+$ (calcd for $C_{18}H_{31}N_2O_6$, 371.21766).

Cystargolide B (2). Pale yellow powder; $[\alpha]^{25}_D$ −28° (c=0.12, MeOH); IR $v_{max}$ 3299, 2964, 1838, 1723, 1648, 1529, 1467, 1157, 1024 $cm^{-1}$; $^1H$ NMR (600 MHz, DMSO-$d_6$) $\delta_H$ 8.53 (NHb, d, 9.0), 8.11 (NHa, d, 8.1), 5.01 (H-2", d, 3.8), 4.38 (H-2', dd 7.7, 7.7), 4.12 (H-2, dd, 6.6, 6.6), 3.51 (H-3", dd, 8.1, 3.9), 2.12 (H-5", m), 2.06 (H-3, m), 2.01 (H-3', m), 1.00 ($H_3$-6", d, 6.7), 0.97 ($H_3$-7", d, 6.5), 0.89 ($H_3$-4, m), 0.88 ($H_3$-5, m), 0.86 ($H_3$-4', m), 0.82 ($H_3$-5', m); $^{13}C$ NMR (150 MHz, DMSO-$d_6$) $\delta_C$ 172.5 (C, C-1), 170.5 (C, C-1'), 169.7 (C, C-4"), 167.0 (C, C-1"), 69.9 (CH, C-2"), 62.5 (CH, C-3"), 57.2 (CH, C-2'), 57.2 (CH, C-2), 30.7 (CH, C-3'), 29.4 (CH, C-3), 26.4 (CH, C-5"), 19.3 ($CH_3$, C-7"), 19.2 ($CH_3$, C-6"), 18.9 ($CH_3$, C-4'), 17.6 ($CH_3$, C-5'), 18.8 ($CH_3$, C-4), 17.7 ($CH_3$, C-5); (+) HRESIMS m/z 357.2021 $[M+H]^+$, (calcd for $C_{17}H_{29}N_2O_6$, 357.20201).

Stereochemical Analysis by Marfey's Method.

Amino acid configurations were determined by Marfey's analysis of hydrolyzed cystargolides A (1) and B (2). 20 µL, of 1 and 2 (10 mg/mL in MeOH) were added to separate microconical vials and then dried. 250 µL of 6M HCl was added to each vial along with a stir bar and heated to 70-80° C. for 75 minutes. Once the reaction mixtures had cooled, 1 mL of 1N $NaHCO_3$ followed by 20 µL, of 1-fluoro-2,4-dinitrophenyl-L-alanine (L-FDAA) (10 mg/mL in acetone) was added to each reaction vial. The reactions were heated at 30-40° C. for 1 hour before quenching with 100 µL, of 6M HCl. The reaction mixture was reduced in volume under air, then diluted to 1 mL with 50:50 $MeOH:H_2O$ for LCMS analysis. 10 µL of derivatized amino acids were analyzed by LC-HRMS with Hypersil Gold 100 Å column (Thermo, 1.9 µm $C_{18}$ 50×2.1 mm). Compounds were eluted using a linear gradient from 95% $diH_2O$/0.1% formic acid (solvent A) and 5% acetonitrile/0.1% formic acid (solvent B) to 60% solvent A and 40% solvent B over 55 minutes followed by a rapid increase to 100% solvent B over 2 minutes then a hold for 3 minutes. A flow rate of 400 µL/min was used. Eluent was detected by ESI-MS monitoring m/z 120-800 in positive mode and UV (200-600 nm). Retention times were compared to that of authentic derivatized standards to determine the amino acid configurations. Retention times of derivatized standards were as follows: L-Val 28.70 min, D-Val 35.03 min, L-Ile 34.02 min, D-Ile 40.44 min, L-allo-Ile 34.27 min and D-allo-Ile 40.52 min.

20S Proteasome Inhibition Assay.

1 and 2 were tested for proteasome inhibition using purified human erythrocyte 20S proteasome (Enzo Life Sciences: BML-PW8720-0020). 20S proteasome was diluted to a final concentration of 3 µg/mL in assay buffer (50 mM Tris/HCl, pH 7.5, 25 mM KCl, 10 mM NaCl, 1 mM $MgCl_2$, and 0.03% SDS), and incubated with inhibitors at varying concentrations at 30° C. for 10 minutes. To determine the chymotrypsin-like activity, the reaction was initiated by the addition of the fluorogenic substrate Suc-LLVY-AMC (Enzo Life Sciences, BML-9802-9090) at a final concentration of 75 µM. The rate of cleavage of the substrate was determined by measuring fluorescence using a Spectra Max M2 (Molecular Devices) plate reader at an excitation wavelength of 360 nm and emission of 460 nm. The fluorescence was recorded every 15 seconds for 30 minutes, and the linear regression between 15 and 30 minutes were used to calculate the rate of substrate cleavage (AFU/s). Control wells were included that contained no inhibitor to show the maximum substrate cleavage rate, epoxomicin (0.5 µM) and no enzyme (Blank) to show the minimum response. The $IC_{50}$ values, the concentration required to reduce the enzyme response by 50 percent, were calculated by Prism 6.0 (GraphPad Software) using a nonlinear regression dose-response, variable slope model based on triplicate measurements±standard deviation.

As described herein, novel β-lactone containing natural products, cystargolides A (1) and B (2), were isolated from the actinomycete *Kitasatospora cystarginea*. The production of these two natural products was highlighted using a methodology associating liquid chromatography-high resolution mass spectrometry (LC-HRMS) analysis and principal component analysis (PCA). Their structures were elucidated by interpretation of NMR experiments and tandem mass spectrometry. The absolute configurations of the amino acid residues were determined using Marfey's method and the relative configurations of the β-lactone substituents were determined based on the vicinal $^3J_{HH}$ coupling value. Due to the presence of the β-lactone, 1 and 2 were evaluated for their ability to inhibit human 20S proteasome; both inhibited the 20S proteasome in vitro with $IC_{50}$ values of 0.35 and 0.93 μM respectively under the conditions tested.

Although the present invention has been disclosed in the form of preferred embodiments and variations thereon, it will be understood that numerous additional modifications and variations could be made thereto without departing from the scope of the invention.

For the sake of clarity, it is to be understood that the use of "a" or "an" throughout this application does not exclude a plurality, and "comprising" does not exclude other steps or elements.

What is claimed is:

1. A cystargolide prodrug compound, the cystargolide prodrug compound comprising an acetate ester derivative of a cystargolide compound having formula I:

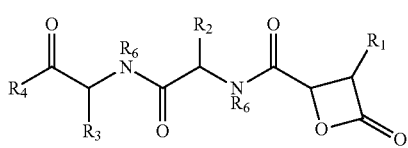

wherein $R_1$ is H or linear or branched $C_1$-$C_6$ lower alkyl; $R_2$ is H, linear or branched $C_1$-$C_6$ lower alkyl, or a proteinogenic amino acid side chain; $R_3$ is H, linear or branched $C_1$-$C_6$ lower alkyl, or a proteinogenic amino acid side chain; $R_4$ is —OH or —O—$R_5$ wherein $R_5$ is linear or branched $C_1$-$C_6$ lower alkyl; and each $R_6$ is independently H or —$CH_3$, wherein the cystargolide prodrug compound comprising the acetate ester derivative is formulated such that upon administration of the cystargolide prodrug compound comprising the acetate ester derivative to a mammal, the cystargolide compound having formula I, or an active metabolite thereof, is provided.

2. The cystargolide prodrug compound of claim 1, wherein the cystargolide compound is:

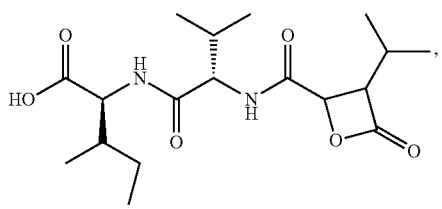 [SMILES: CCC(C)[C@H](NC(=O)[C@@H](NC(=O)C1OC(=O)C1C(C)C)C(C)C)C(=O)O]

or an active metabolite thereof.

3. The cystargolide prodrug compound of claim 1, wherein the cystargolide compound is:

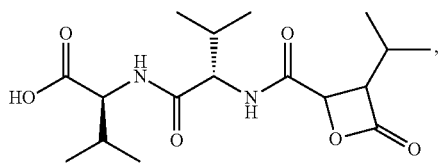 [SMILES: CC(C)C1C(=O)OC1C(=O)N[C@H](C(=O)N[C@H](C(=O)O)C(C)C)C(C)C]

or an active metabolite thereof.

4. A composition comprising a cystargolide prodrug compound of any one of claims 1-3, and a pharmaceutically acceptable carrier, diluent, or excipient.

5. A method of inhibiting 20S proteasome, comprising:
administering a therapeutically effective amount of a composition comprising a compound having a chemical formula:

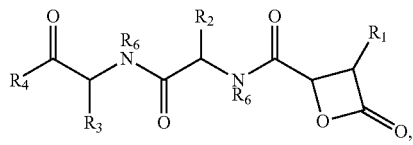

wherein $R_1$ is H or linear or branched $C_1$-$C_6$ lower alkyl; $R_2$ is H, linear or branched $C_1$-$C_6$ lower alkyl, or a proteinogenic amino acid side chain; $R_3$ is H, linear or branched $C_1$-$C_6$ lower alkyl, or a proteinogenic amino acid side chain; $R_4$ is —OH or —O—$R_5$ wherein $R_5$ is linear or branched $C_1$-$C_6$ lower alkyl; and each $R_6$ is independently H or —$CH_3$, or a pharmaceutically acceptable salt or ester thereof.

6. The method of claim 5, wherein the compound has a chemical formula of

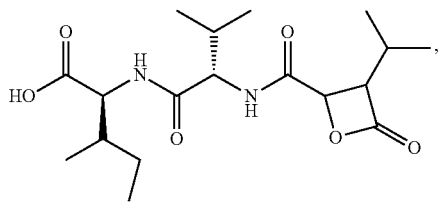 [SMILES: CCC(C)[C@H](NC(=O)[C@@H](NC(=O)C1OC(=O)C1C(C)C)C(C)C)C(=O)O]

or a pharmaceutically acceptable salt or ester thereof.

7. The method of claim 5, wherein the compound has a chemical formula of

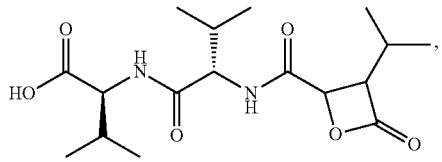

or a pharmaceutically acceptable salt or ester thereof.

8. The method of claim 5, wherein the composition further comprises at least one of a pharmaceutically acceptable carrier, diluent, and excipient.

9. The method of claim 6, wherein the composition further comprises at least one of a pharmaceutically acceptable carrier, diluent, and excipient.

10. The method of claim 7, wherein the composition further comprises at least one of a pharmaceutically acceptable carrier, diluent, and excipient.

* * * * *